United States Patent [19]

Hinchliffe

[11] Patent Number: 5,586,986

[45] Date of Patent: Dec. 24, 1996

[54] INSTRUMENT FOR CLOSING TROCAR PUNCTURE WOUNDS

[75] Inventor: Peter W. J. Hinchliffe, New Haven, Conn.

[73] Assignee: United States Surgical Corporation, Norwalk, Conn.

[21] Appl. No.: 393,541

[22] Filed: Feb. 23, 1995

Related U.S. Application Data

[63] Continuation of Ser. No. 91,793, Jul. 14, 1993.

[51] Int. Cl.⁶ .................................................. A61B 17/00
[52] U.S. Cl. ........................ 606/147; 606/144; 606/222; 112/169; 223/104
[58] Field of Search ...................... 606/144–148, 606/139, 151, 222–227; 112/169, 80.03; 223/102, 104

[56] References Cited

U.S. PATENT DOCUMENTS

| | | |
|---|---|---|
| 373,372 | 11/1887 | La Forest King ...................... 606/146 |
| 1,037,864 | 9/1912 | Carlson et al. . |
| 1,449,087 | 3/1923 | Hugbee . |
| 1,822,330 | 9/1931 | Ainslie . |
| 2,108,206 | 3/1937 | Meeker . |
| 2,213,830 | 12/1938 | Anastasi . |
| 2,579,192 | 12/1951 | Kohl . |
| 2,601,564 | 7/1953 | Smith . |
| 2,737,954 | 2/1954 | Knapp . |
| 2,959,172 | 11/1960 | Held . |
| 3,090,386 | 7/1961 | Curtis . |
| 3,168,097 | 7/1961 | Dormia . |
| 3,470,875 | 10/1966 | Johnson . |

(List continued on next page.)

FOREIGN PATENT DOCUMENTS

| | | |
|---|---|---|
| 140557 | 5/1985 | European Pat. Off. . |
| 0478949 | 4/1992 | European Pat. Off. . |
| 2740274 | 3/1978 | Germany . |
| 9112301 | 11/1991 | Germany . |
| 4137218 | 11/1993 | Germany . |
| 1093329 | 5/1984 | U.S.S.R. . |
| WO92/12674 | 8/1992 | WIPO . |
| WO93/01750 | 2/1993 | WIPO . |
| WO94/05213 | 3/1994 | WIPO . |

OTHER PUBLICATIONS

REMA Brochure, REMA–Medizintechnik GmbH, 1992.
European Search Report for European Patent Application No. EP 94 11 0995.

*Primary Examiner*—Gary Jackson
*Assistant Examiner*—Jeffrey A. Schmidt

[57] ABSTRACT

A surgical instrument for applying sutures including an elongated housing having a proximal end and a distal end, means associated with the distal end of the elongated housing for carrying at least one needle, the needle carrier means being movable between a retracted position and an extended position, at least one needle positioned on the needle carrier means, and means associated with the needle carrier means for moving the needle carrier means to the extended position to deploy the at least one needle such that upon movement of the needle carrier means by the moving means, the needle carrier moves from the retracted position to the extended position whereby the at least one needle is caused to travel through a tissue engaging path in one continuous motion. Another embodiment of the surgical instrument of the present invention for applying sutures includes an elongated housing having a proximal end and a distal end and means associated with the distal end of the elongated housing, for carrying and deploying at least two needles at a predetermined distance from each other, the carrying and deploying means being rotatable out of a first plane corresponding to a retracted position and into a second plane corresponding to an extended position while maintaining the at least two needles at the predetermined distance from each other. The instrument preferably further includes at least one needle retaining means associated with the elongated housing for receiving and retaining the at least two needles. The needle retaining means may include a pair of needle receiving pockets disposed within the elongated housing. The needle receiving pockets may be filled with a compliant material or a latch mechanism.

18 Claims, 17 Drawing Sheets

U.S. PATENT DOCUMENTS

| | | |
|---|---|---|
| 3,807,407 | 3/1974 | Schweizer . |
| 3,871,379 | 3/1975 | Clarke . |
| 3,901,244 | 8/1975 | Schweizer . |
| 3,946,740 | 3/1976 | Bassett . |
| 4,027,608 | 6/1977 | Arbuckle . |
| 4,103,690 | 8/1978 | Harris . |
| 4,345,601 | 8/1982 | Fukuda . |
| 4,493,323 | 1/1985 | Albright et al. . |
| 4,510,934 | 4/1985 | Batra . |
| 4,557,265 | 12/1985 | Andersson . |
| 4,597,390 | 7/1986 | Mulhollan et al. . |
| 4,602,635 | 7/1986 | Mulhollan et al. . |
| 4,614,187 | 9/1986 | Mulhollan et al. . |
| 4,621,640 | 11/1986 | Mulhollan et al. . |
| 4,635,638 | 1/1987 | Weintraub et al. . |
| 4,676,243 | 6/1987 | Clayman . |
| 4,827,931 | 5/1989 | Longmore . |
| 4,836,205 | 6/1989 | Barrett . |
| 4,852,568 | 8/1989 | Kensey . |
| 4,890,615 | 1/1990 | Caspari et al. . |
| 4,923,461 | 5/1990 | Caspari et al. . |
| 4,935,027 | 6/1990 | Yoon . |
| 4,957,498 | 9/1990 | Caspari et al. . |
| 4,963,147 | 10/1990 | Agee et al. . |
| 4,971,067 | 11/1990 | Bolduc et al. . |
| 4,986,825 | 1/1991 | Bays et al. . |
| 5,037,433 | 8/1991 | Wilk et al. . |
| 5,047,039 | 9/1991 | Avant et al. . |
| 5,129,912 | 7/1992 | Noda et al. . |
| 5,152,769 | 10/1992 | Baber . |
| 5,188,636 | 2/1993 | Fedotov . |
| 5,222,508 | 6/1993 | Contarini . |
| 5,308,353 | 5/1994 | Beurrier . |
| 5,320,632 | 6/1994 | Heidmueller . |
| 5,336,239 | 8/1994 | Gimpelson ............................. 606/223 |
| 5,350,385 | 9/1994 | Christy ..................................... 606/146 |
| 5,368,601 | 11/1994 | Sauer et al. . |
| 5,374,275 | 12/1994 | Bradley et al. ......................... 606/144 |
| 5,403,328 | 4/1995 | Shallman . |
| 5,403,329 | 4/1995 | Hinchcliffe ............................. 606/144 |

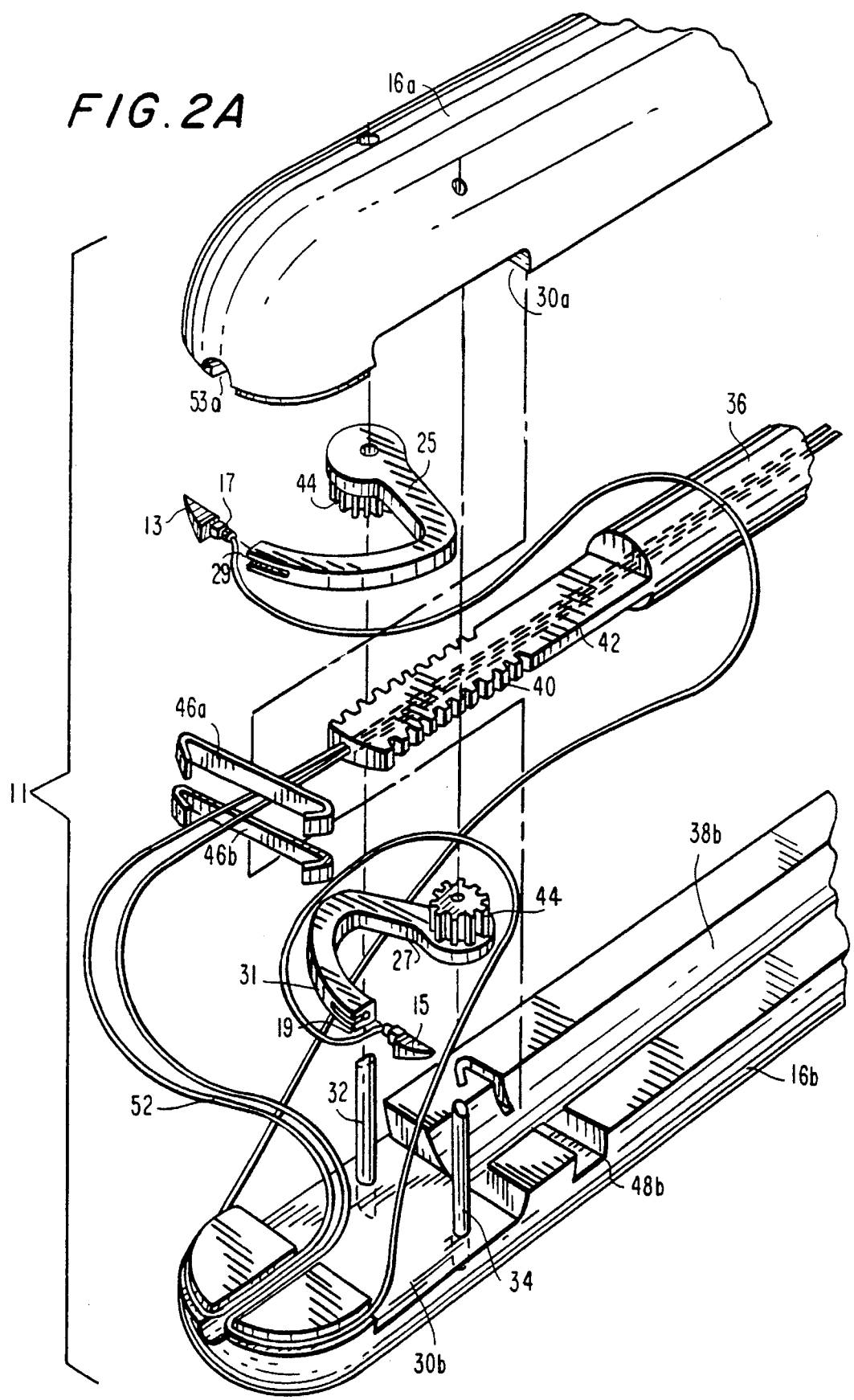

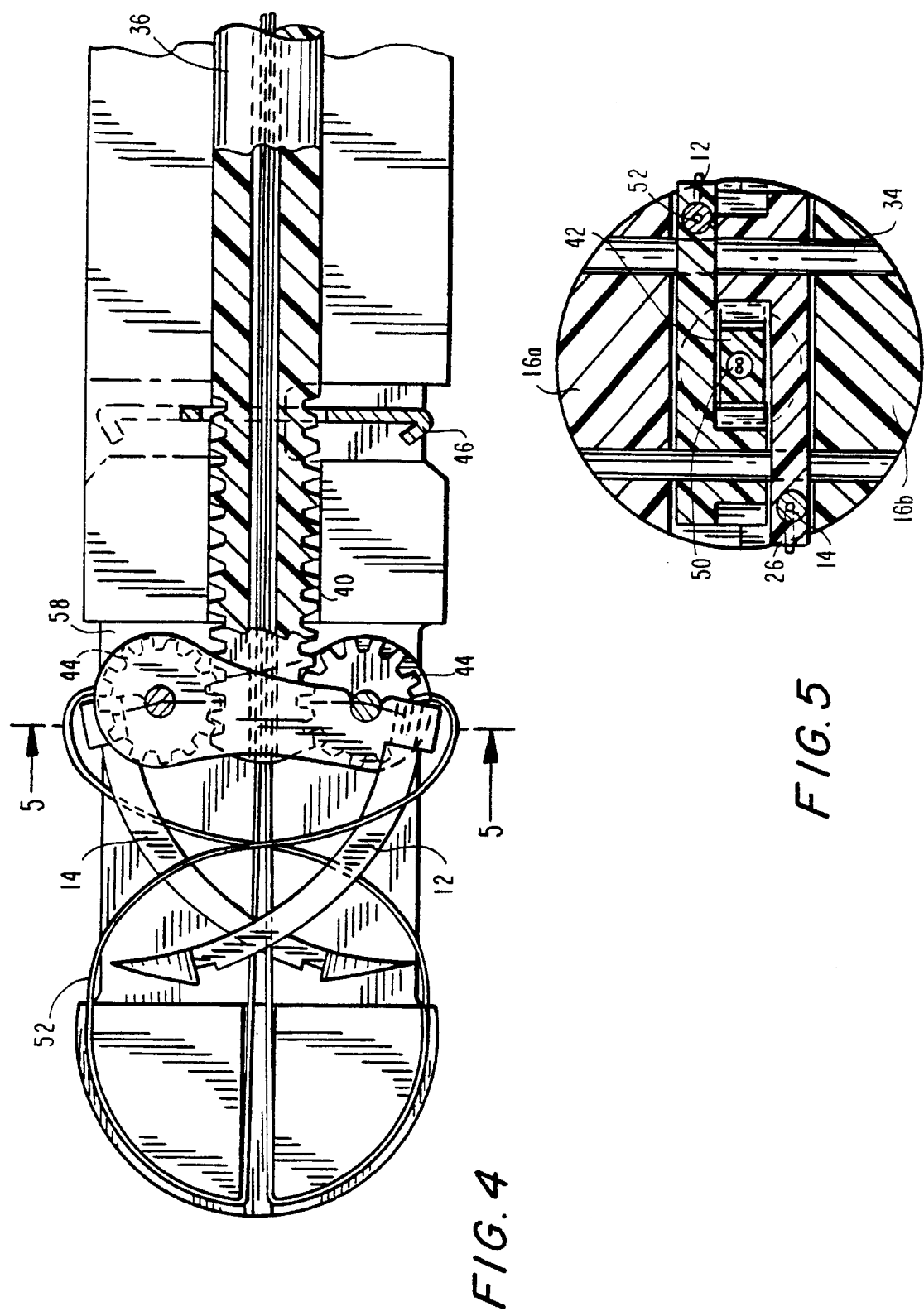

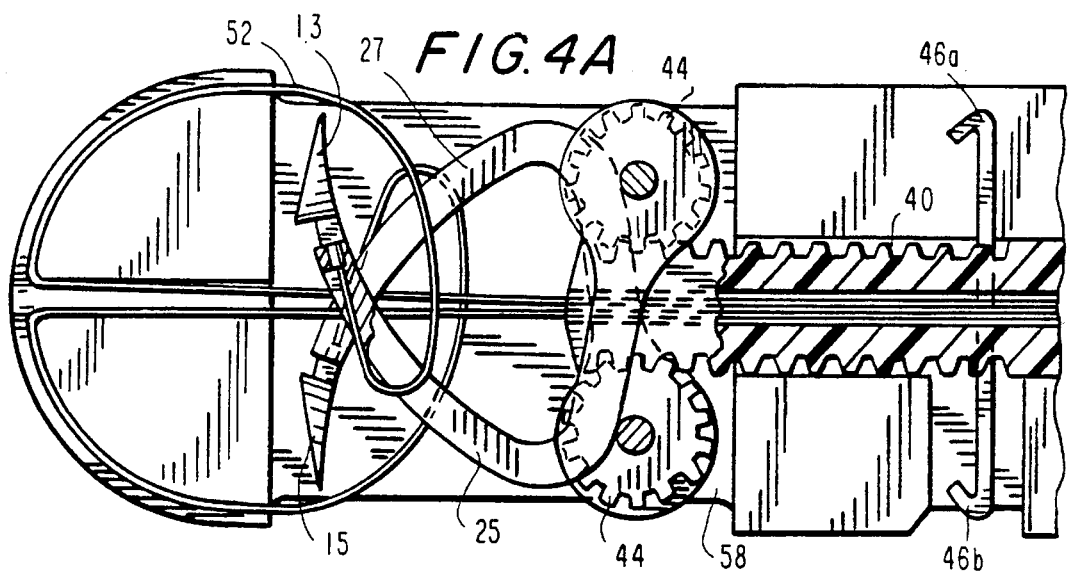
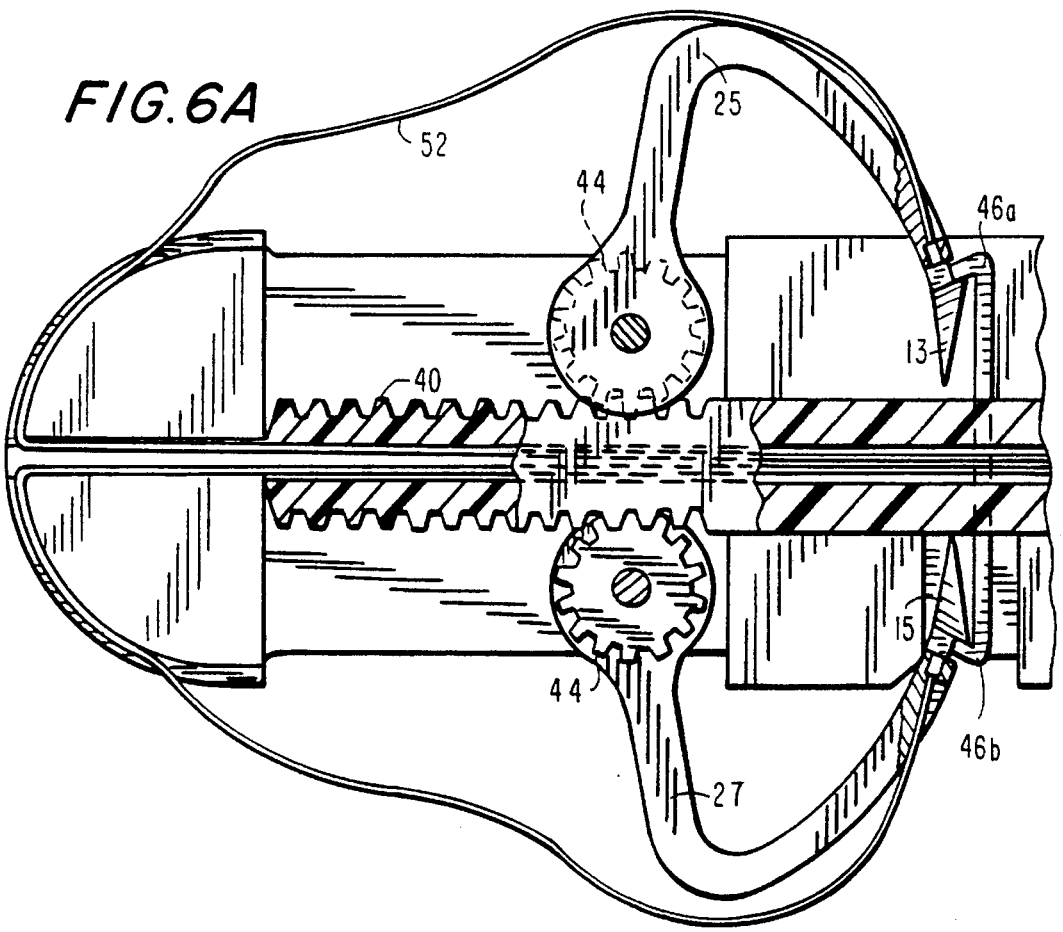

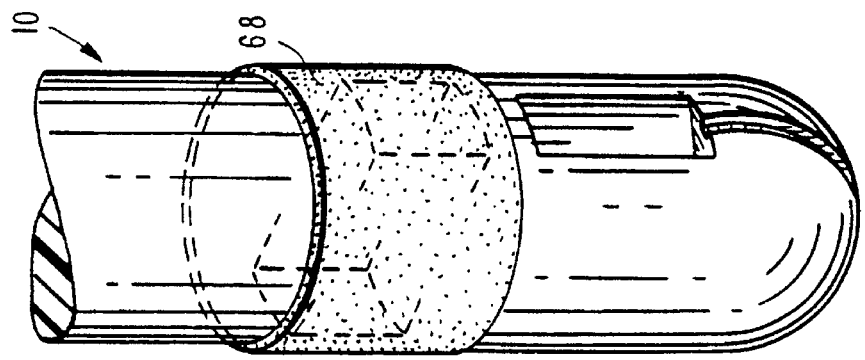
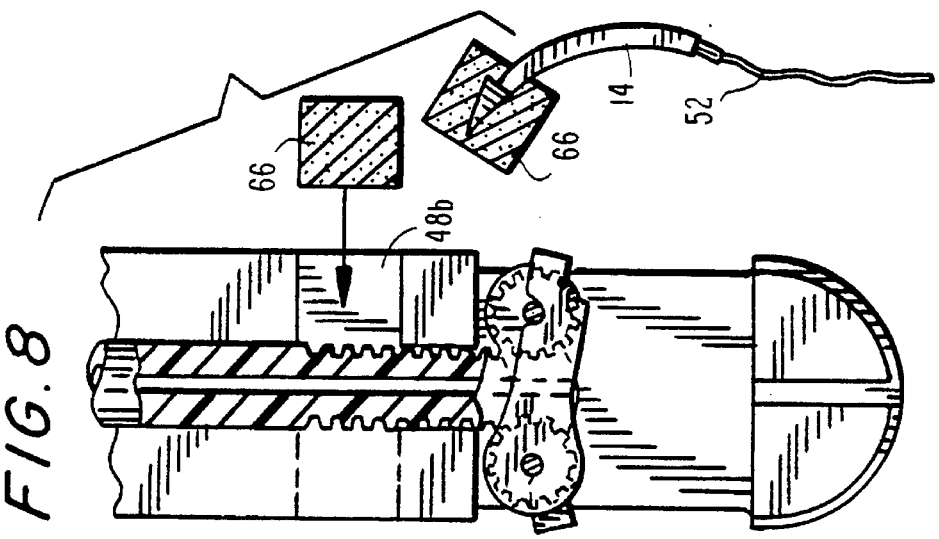
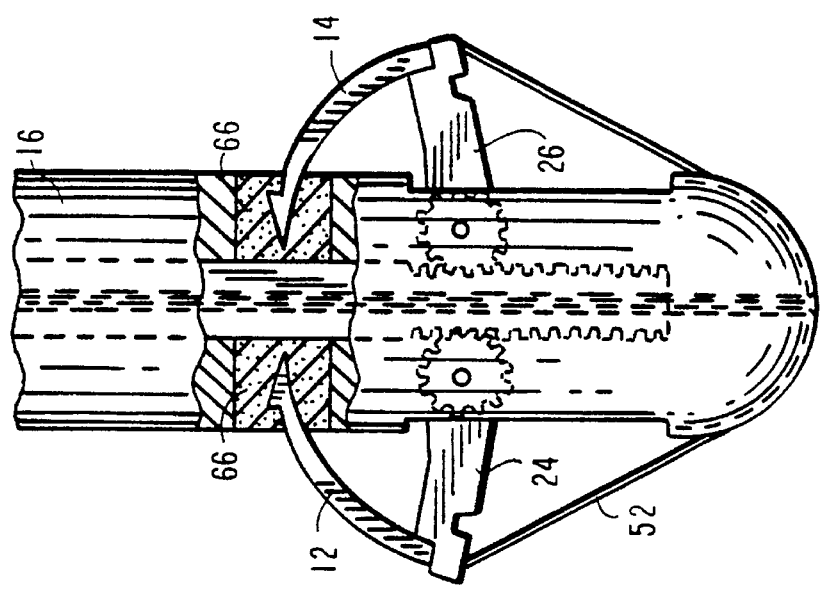

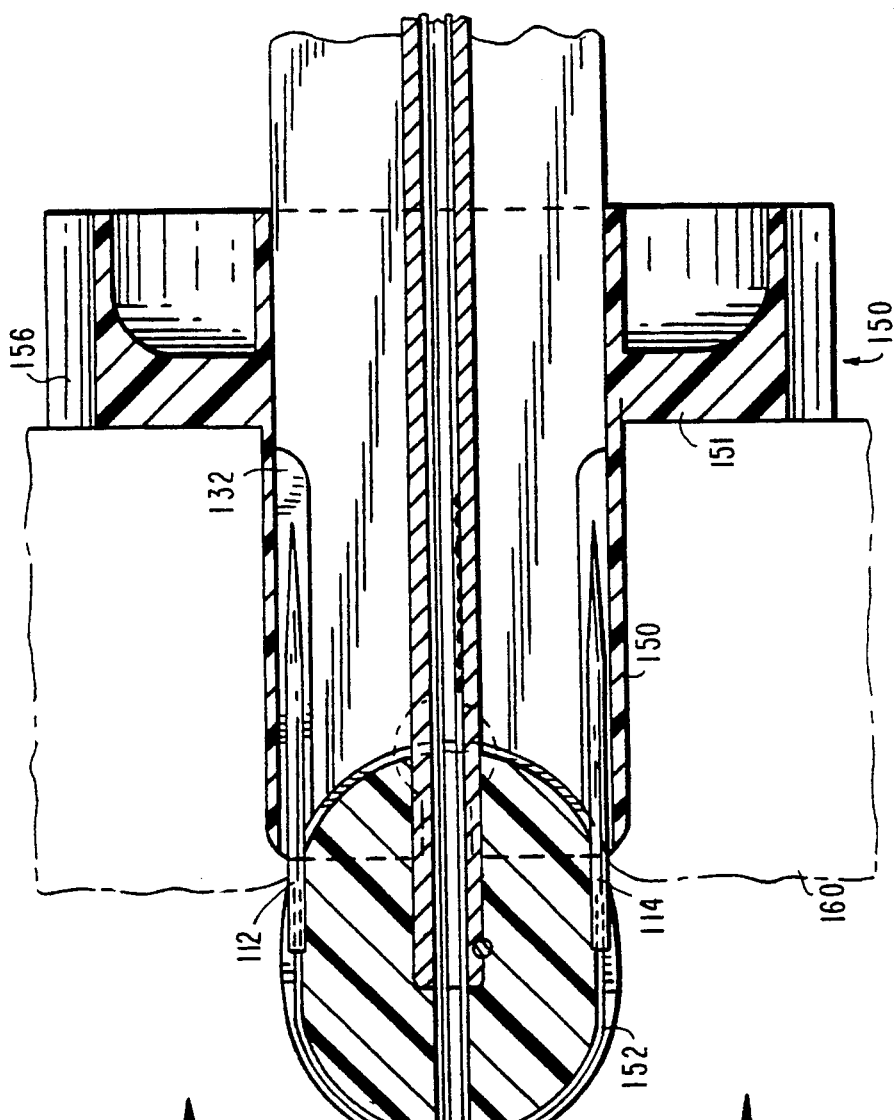
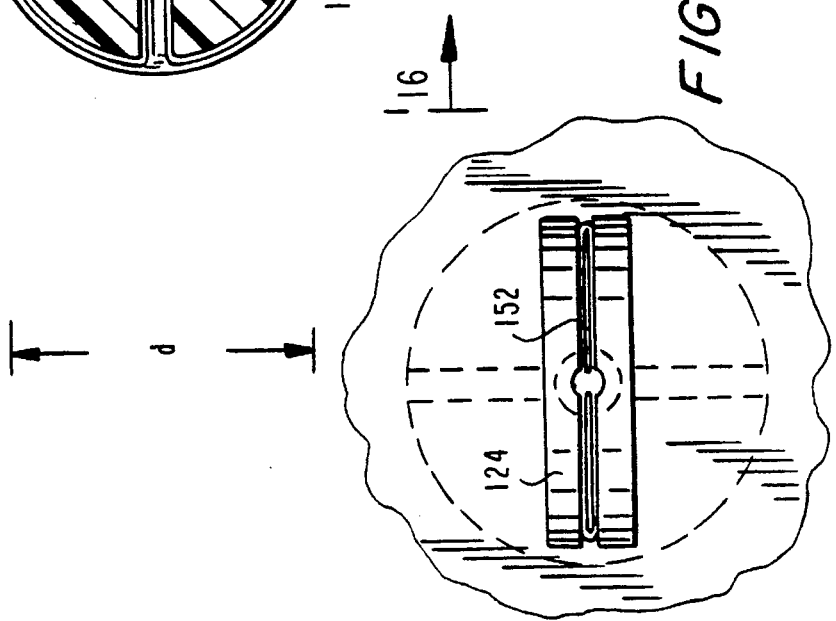
FIG. 15
FIG. 16

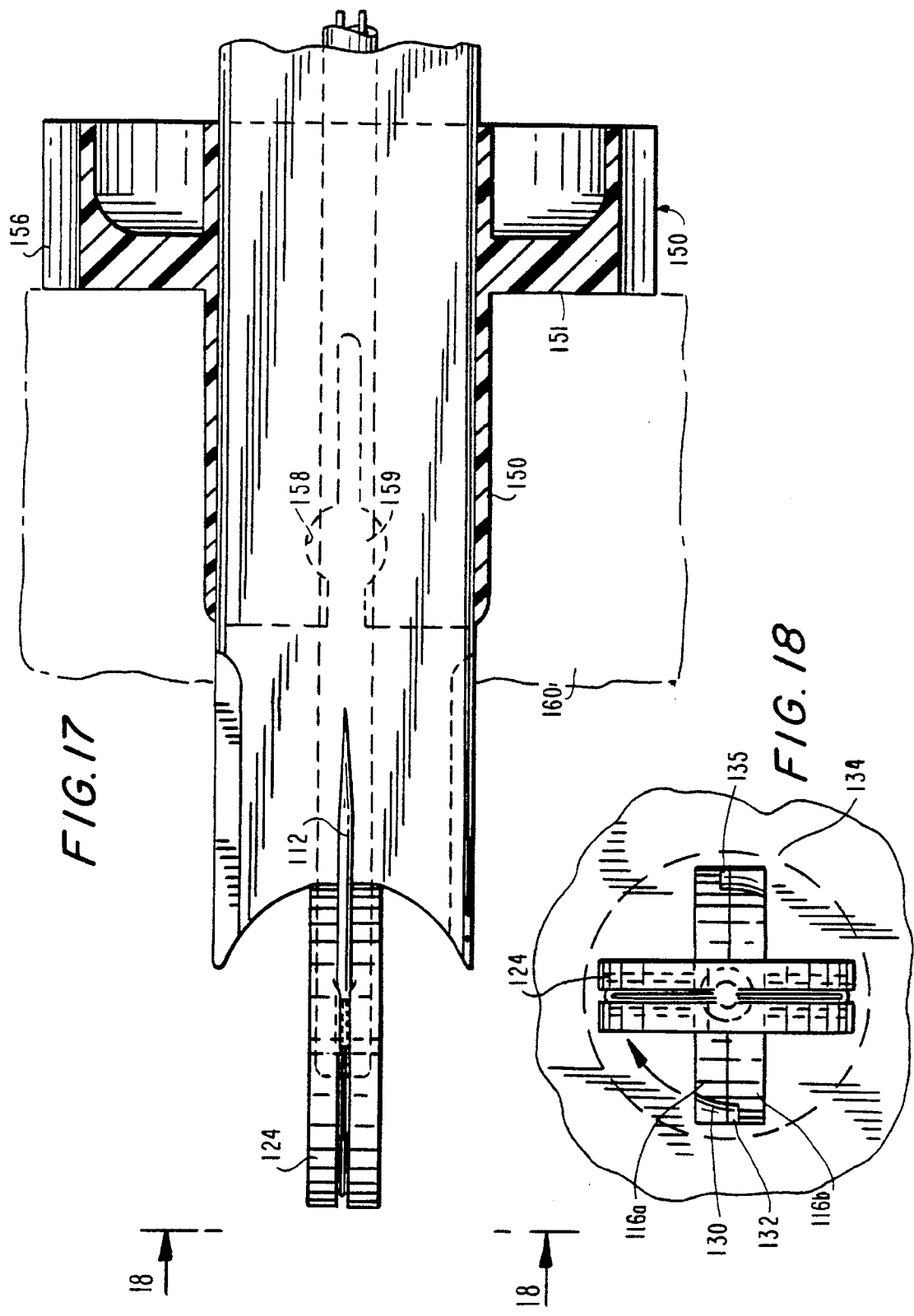

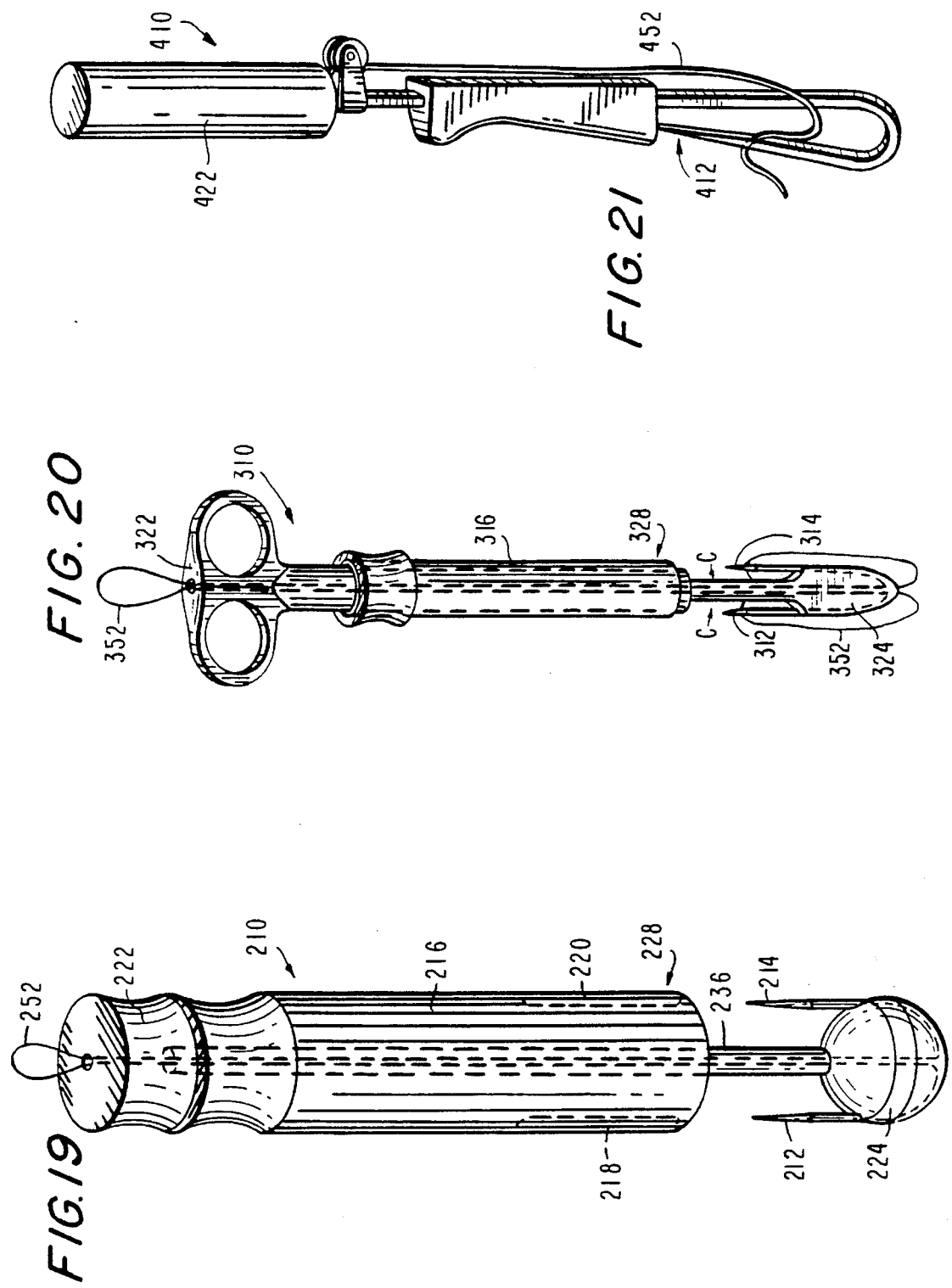

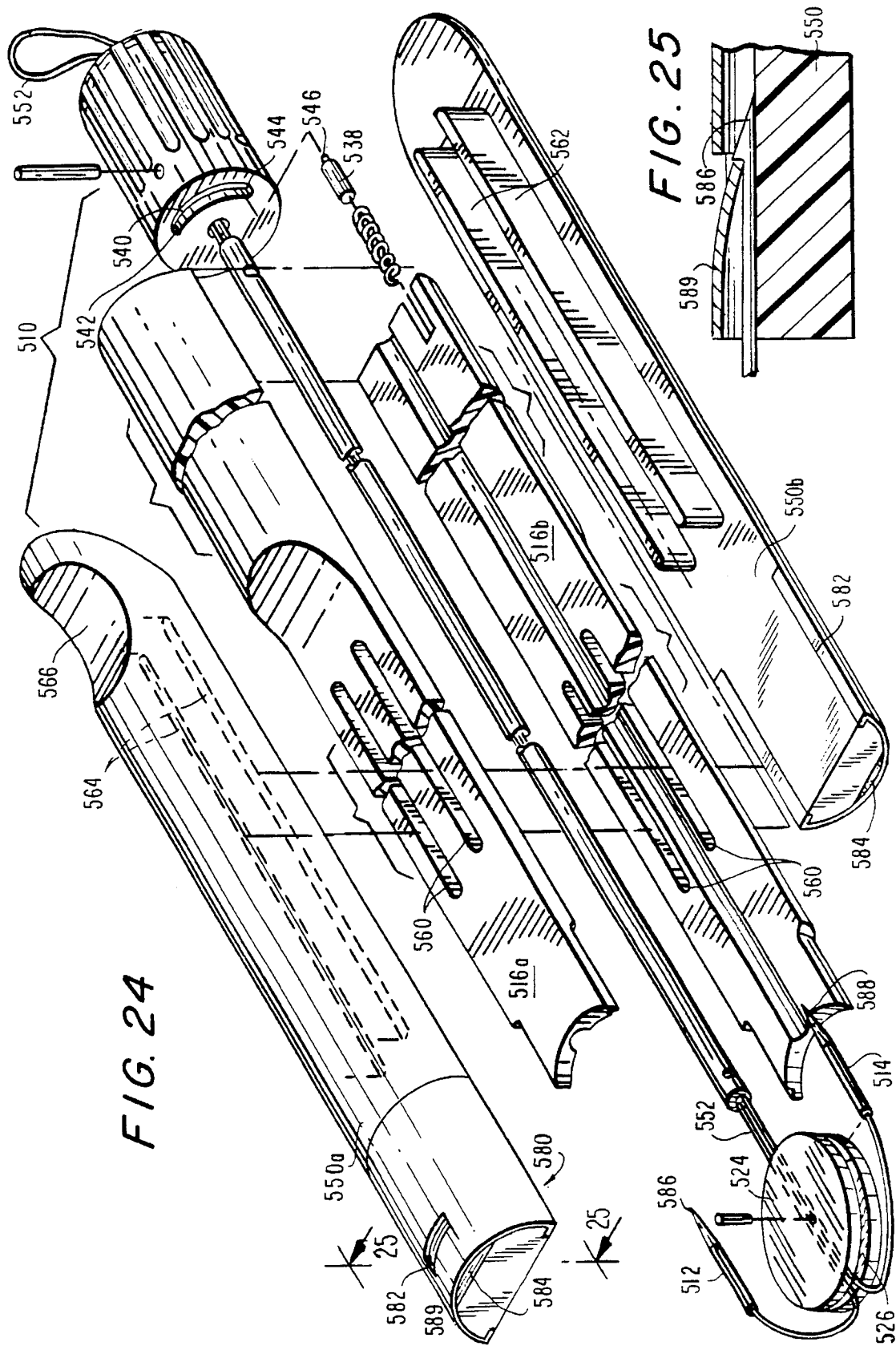

INSTRUMENT FOR CLOSING TROCAR PUNCTURE WOUNDS

This is a continuation of copending application Ser. No. 08/091,793 filed Jul. 14, 1993.

BACKGROUND OF THE INVENTION

1. Field of the Invention

This invention relates to instruments for suturing puncture wounds and more particularly to instruments for closing trocar puncture wounds formed during endoscopic surgical procedures.

2. Description of the Related Art

With laparoscopic and endoscopic surgery, a small incision or puncture is made in the patient's body to provide access for a tube or a cannula device. Once extended into the patient's body, the cannula allows for insertion of various surgical instruments such as scissors, dissectors, retractors, or biopsy instruments to perform diagnostics and/or surgery. Upon completion of the surgical procedure, the remaining trocar wound may require some attention, e.g., in the form of placing sutures to close the wound. In certain cases it may be desirable to close the wound from within.

A device which forms sutures from within the urethra is shown in Soviet Patent SU 1093329. The device is inserted into the urethra and pivotally deploys needles from which sutures are subsequently pulled through the side walls of the urethra.

Other devices have been developed which are used to place sutures from within a wound. For example, co-pending commonly assigned applications Ser. No. 07/950,073 filed Sep. 23, 1992 and Ser. No. 08/013,244 filed Feb. 23, 1993 as well as co-pending application Ser. No. 07/876,511 relate to different surgical instruments for placing sutures from within a trocar wound. Also, a device has been developed for placing sutures from within a trocar wound which includes a needle clamping device for capturing the needles upon deployment thereof. Such a device is shown in a product brochure of REMA-Medizintechnik GmbH of Germany.

Accordingly, a need exists, for an improved instrument which provides better deployment and capturing or shielding of the needles.

SUMMARY OF THE INVENTION

The present invention provides a novel surgical instrument for applying sutures through body tissue and includes a lightweight and easy to use instrument which may be operated quickly and efficiently.

The instrument includes an elongated housing having a proximal end and a distal end, means associated with the distal end of the elongated housing for carrying at least one needle, the needle carrier means being movable between a retracted position and an extended position, at least one needle positioned on the needle carrier mess, and means associated with the needle carrier means for moving the needle carrier means to the extended position to deploy the at least one needle such that upon movement of the needle carrier means by the moving means, the needle carrier moves from the retracted position to the extended position whereby the at least one needle is caused to travel through a tissue engaging path in one continuous motion.

In one embodiment, the moving means are slidably disposed within the elongated housing and operable from the proximal end thereof and the needle carrier means are rotatably disposed within the elongated housing. Preferably, the needle carrier means includes at least one arm member adapted for holding the at least one needle. The arm member may be adapted for releasably holding the at least one needle.

The instrument may further comprise means associated with the elongated housing for receiving and retaining the at least one needle. The receiving and retaining means is preferably disposed at a fixed distance with respect to the distal end of the elongated housing. In one embodiment, the receiving and retaining means includes a latch member. In another embodiment, the receiving and retaining means includes a compliant material such that the at least one needle becomes retained within the compliant material upon travel of the at least one needle through the tissue engaging path.

The carrying and deploying means may further include an elongated actuator rod operatively associated with the at least one needle carrier, such that the elongated actuator rod is operable from the proximal end of the elongated housing to control movement of the at least one needle carrier. In one embodiment, the elongated actuator rod is preferably slidably disposed within the elongated housing.

Another embodiment of the surgical instrument of the present invention for applying sutures includes an elongated housing having a proximal end and a distal end and means associated with the distal end of the elongated housing, for carrying and deploying at least two needles at a predetermined distance from each other, the carrying and deploying means being rotatable out of a first plane corresponding to a retracted position and into a second plane corresponding to an extended position while maintaining the at least two needles at the predetermined distance from each other. The instrument preferably further includes at least one needle retaining means associated with the elongated housing for receiving and retaining the at least two needles. The needle retaining means may include a pair of needle receiving pockets disposed within the elongated housing. The needle receiving pockets may be filled with a compliant material.

An actuator member is preferably provided which is operatively associated with the carrying and deploying means such that the actuator member is operable from the proximal end of the elongated housing. The actuator member is further preferably rotatably mounted within the elongated housing.

In one particular embodiment, the actuator member is operable between a first position and a second position, and the surgical instrument further comprises a lockout mechanism for releasably retaining the actuator member at each of the first and the second positions.

Another embodiment of the surgical instrument for applying sutures comprises an elongated housing having a proximal end and a distal end, means associated with the elongated housing, for carrying and deploying at least one needle, the needle carrying and deploying means being movable between a retracted position and an extended position and resilient retaining means associated with the elongated housing for receiving and retaining the at least one needle.

BRIEF DESCRIPTION OF THE DRAWINGS

Preferred embodiments of the invention are described hereinbelow with reference to the drawings wherein.

3

Figure 1:
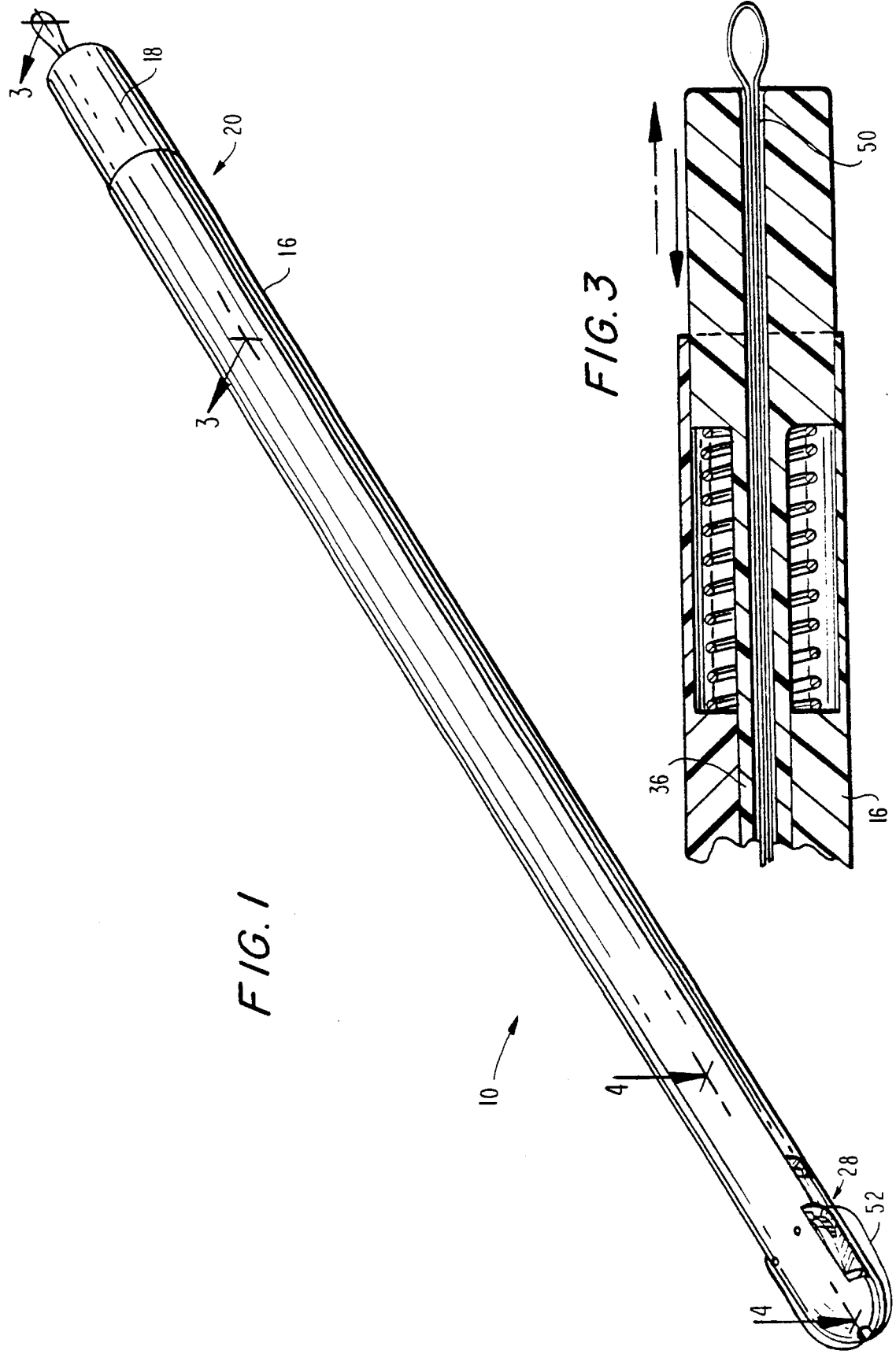
FIG. 1 is a perspective view of one embodiment of the instrument of the present invention.
Figure 2:
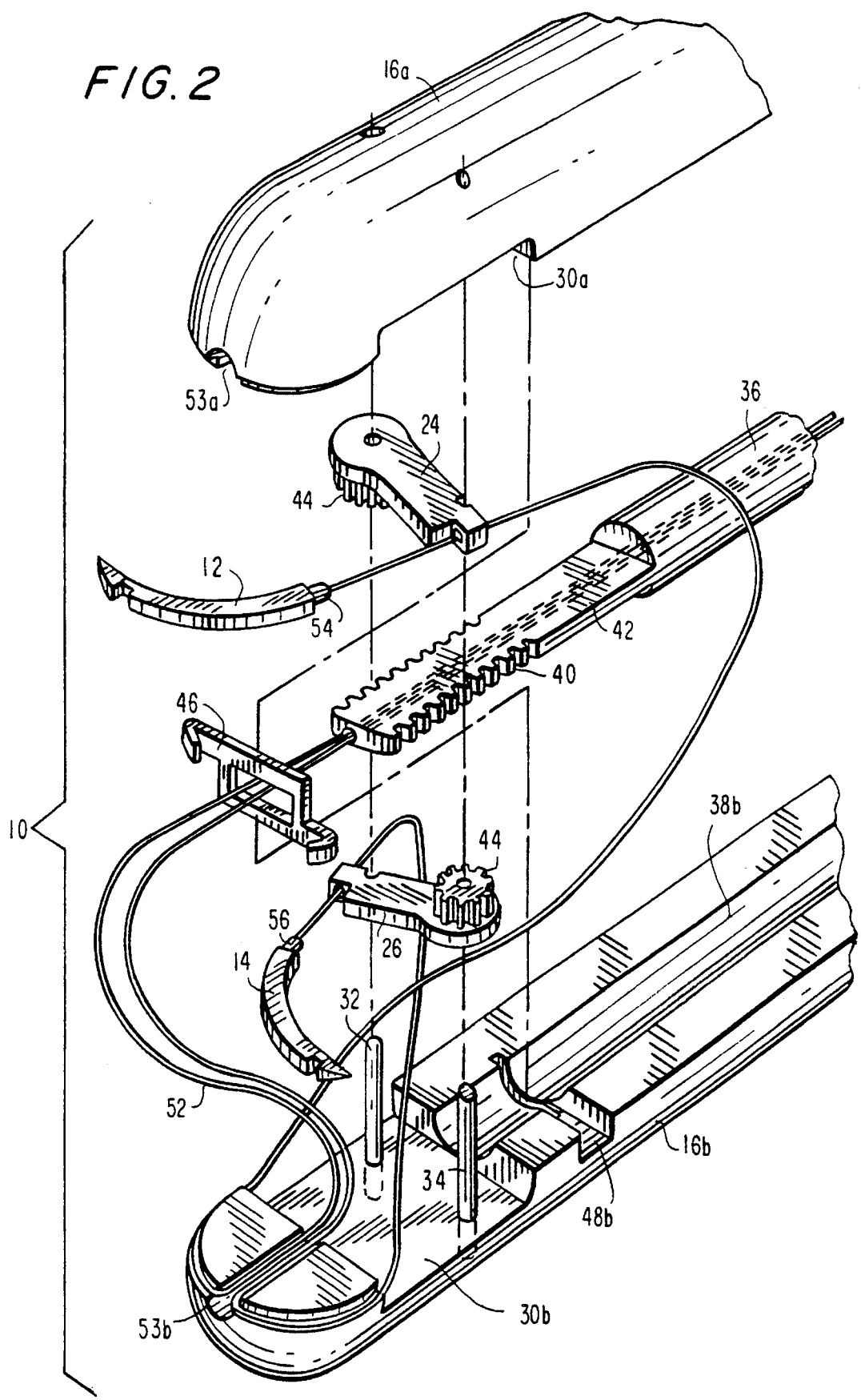
Figure 6:
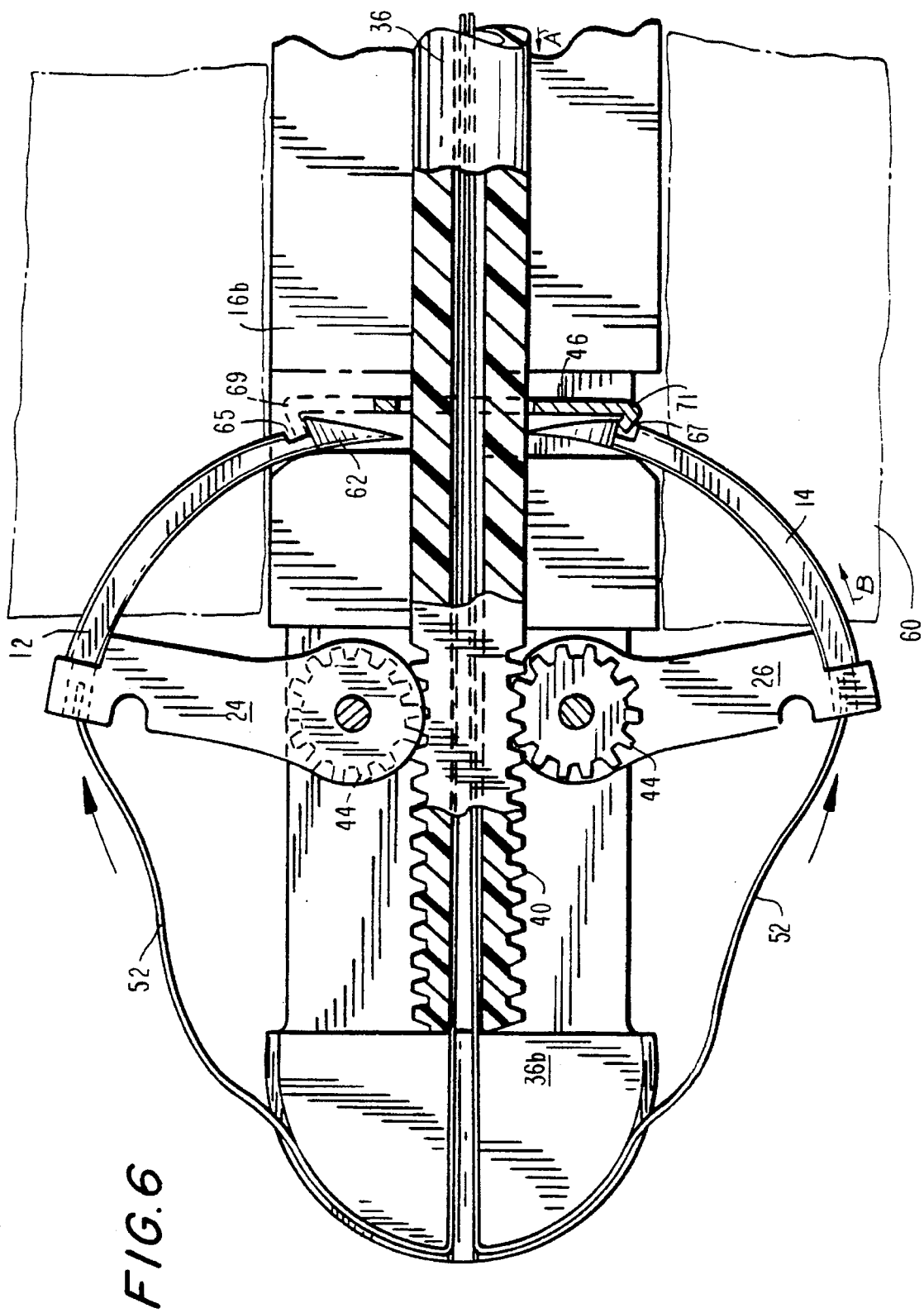
Figure 7A:
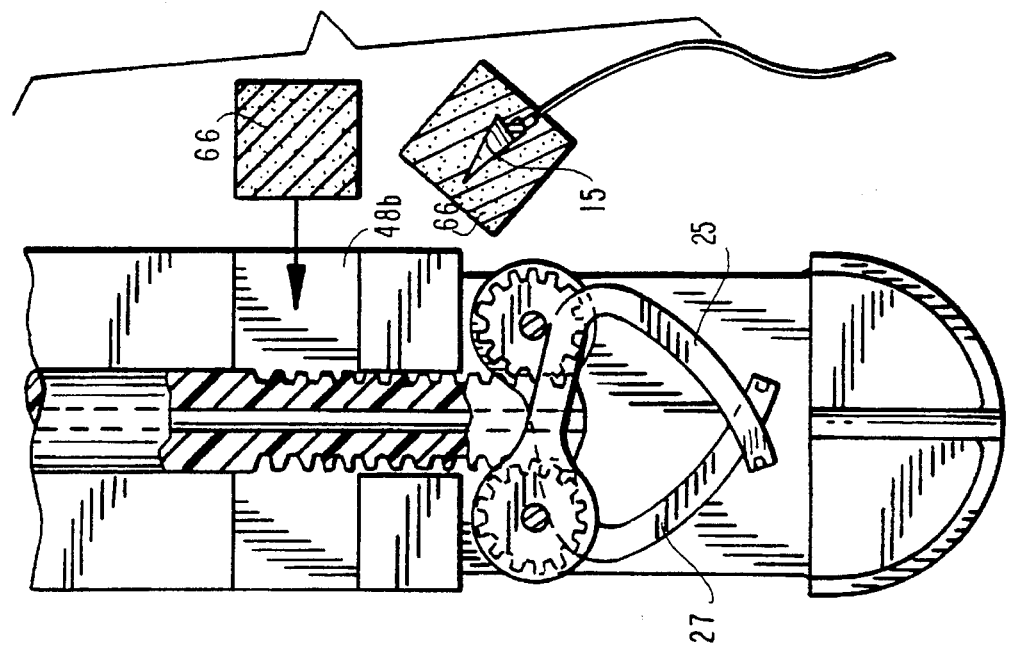
Figure 8A:
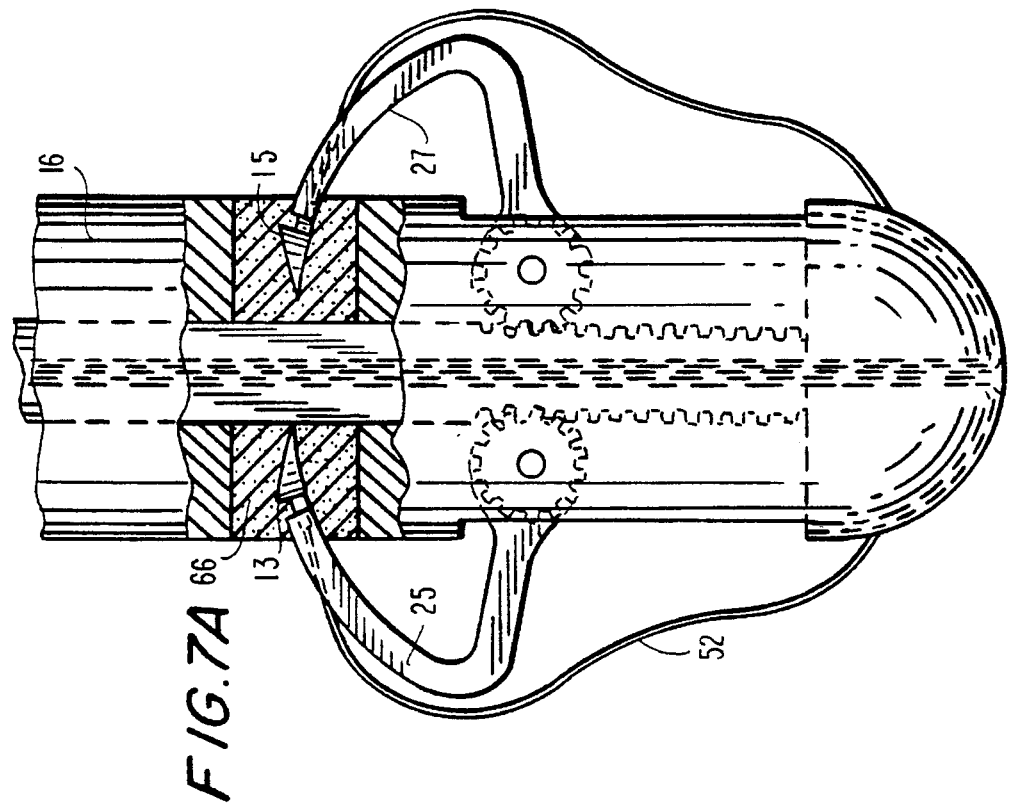
Figure 10:
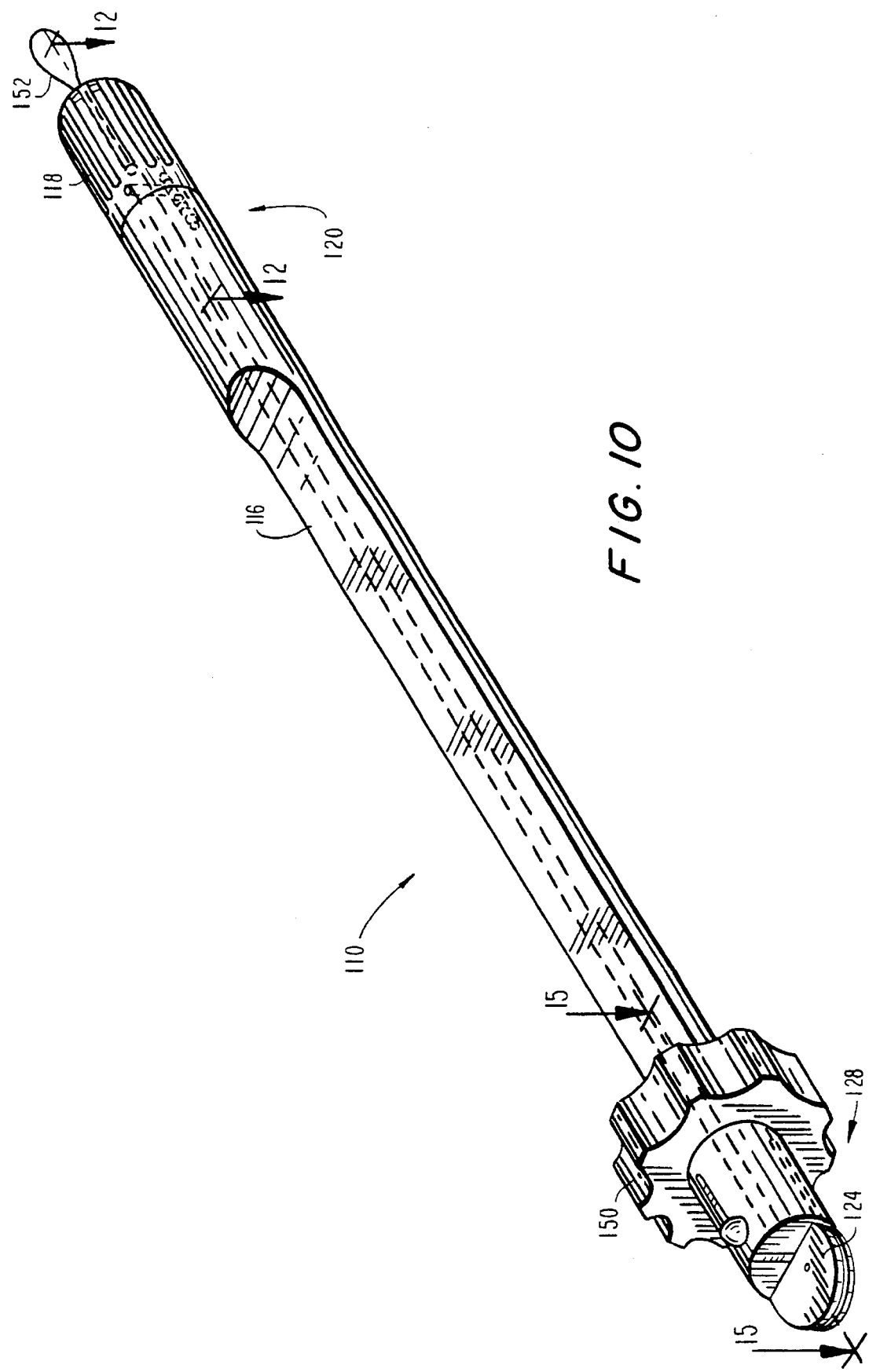
Figure 11:
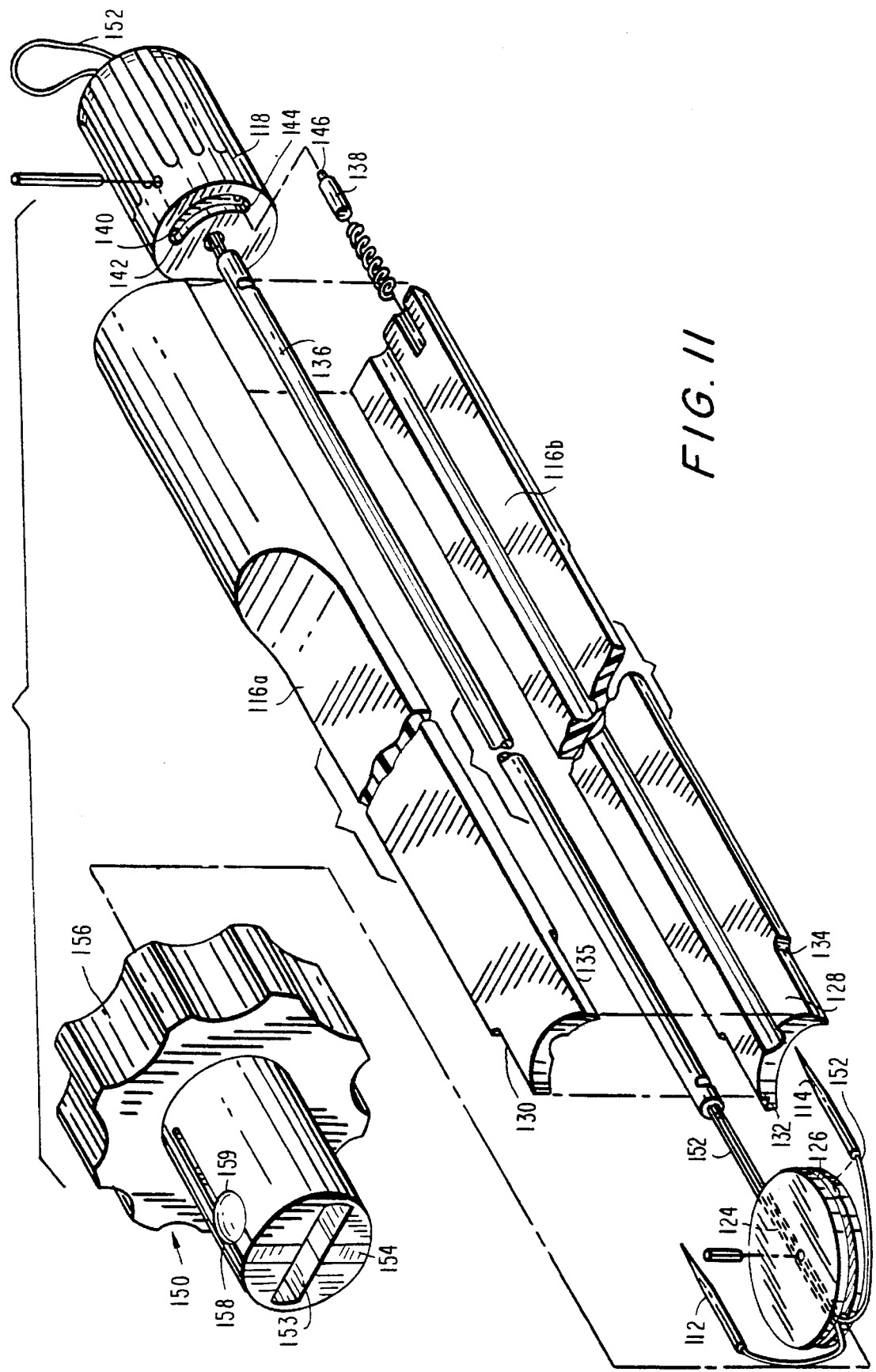
Figure 12:
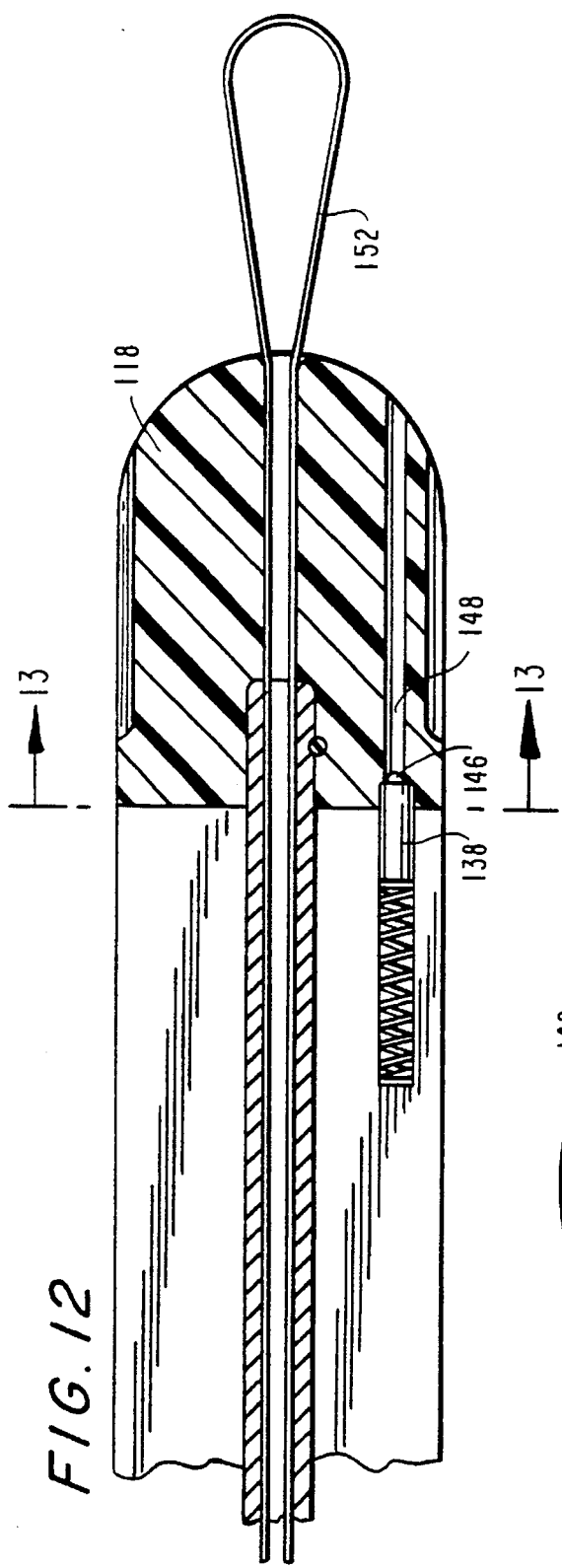
Figure 14:
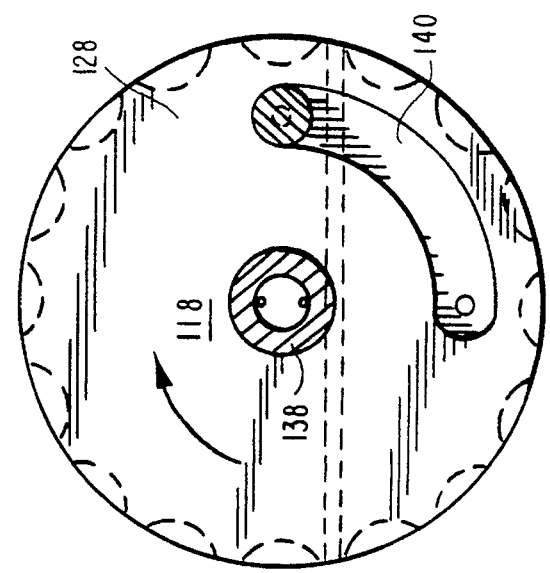
Figure 13:
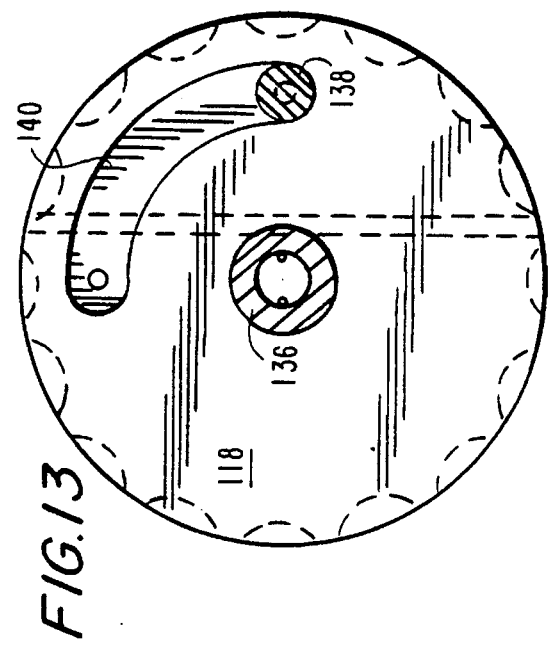
Figure 22:
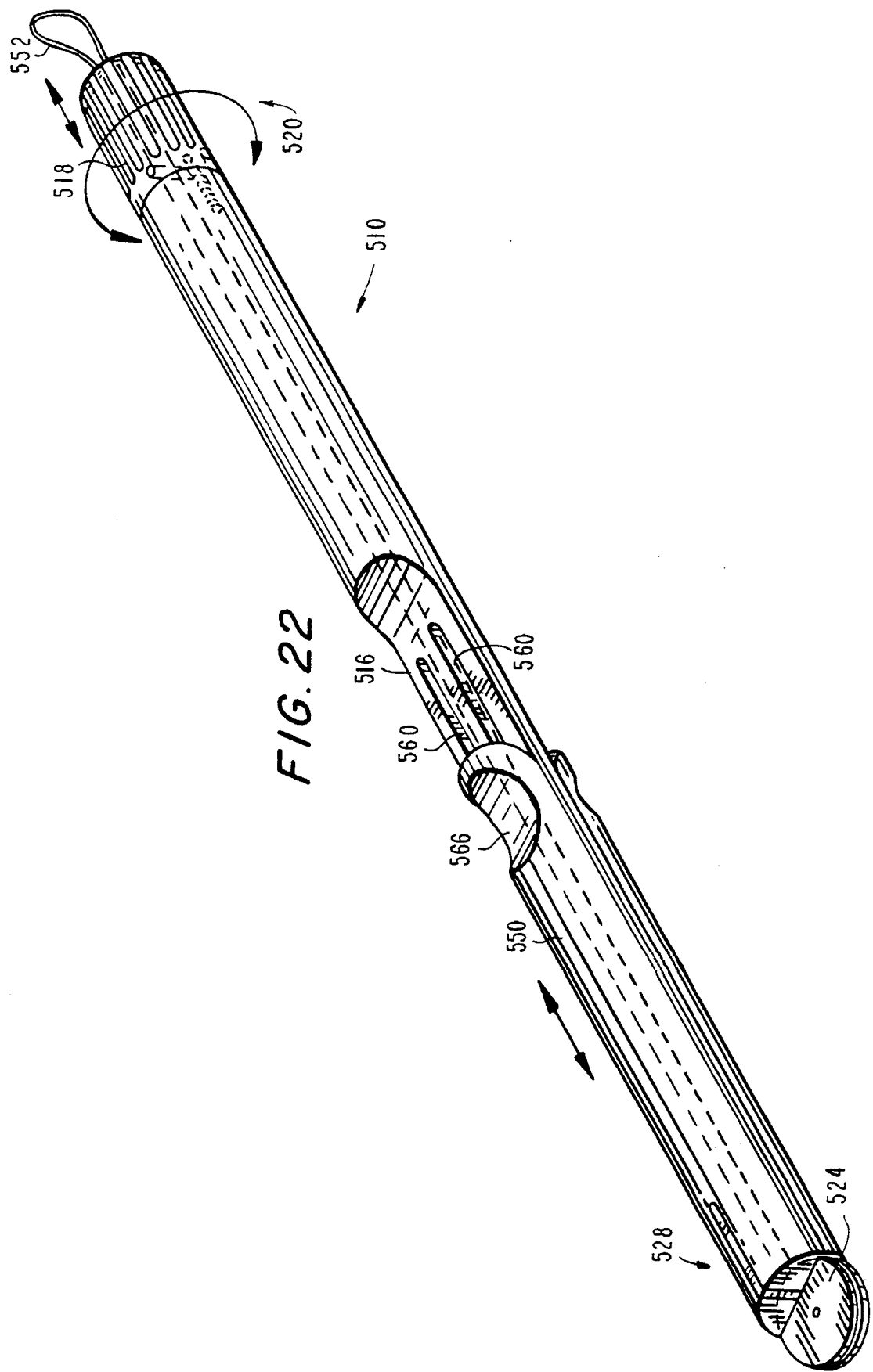
Figure 23:
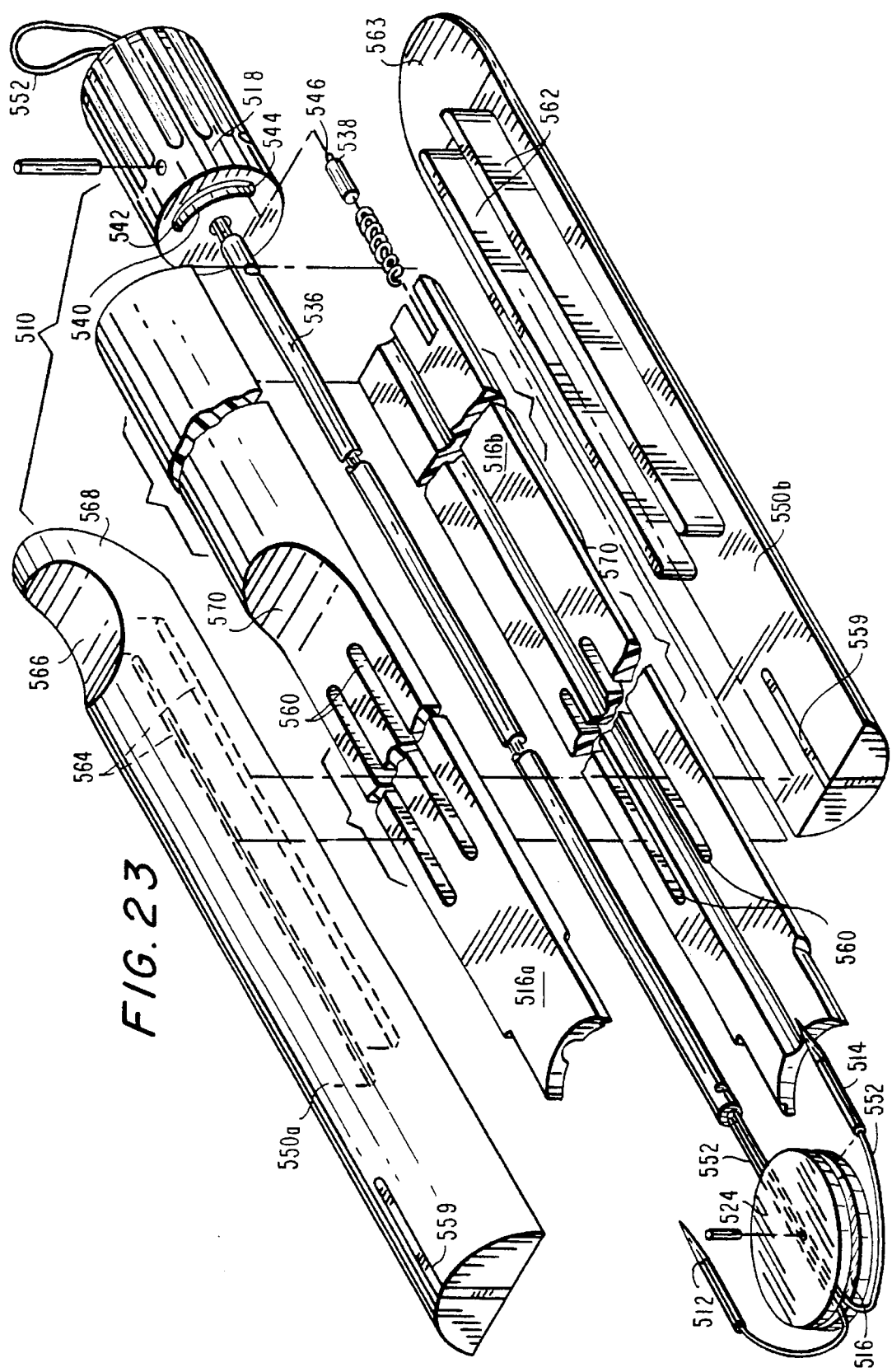

FIG. 2 is an exploded partial-view with parts separated of the distal end of the instrument of FIG. 1;

FIG. 2A is an exploded partial-view with parts separated of the distal end of another embodiment of the instrument of the present invention;

FIG. 3 is a cross-sectional view taken along section line 3—3 of FIG. 1;

FIG. 4 is a cross-sectional view taken along section line 4—4 of FIG. 1;

FIG. 4A is a cross-sectional similar to that of FIG. 4, except an alternative needle structure is illustrated;

FIG. 5 is a cross-sectional view taken along line 5—5 of FIG. 4;

FIG. 6 is a view similar to FIG. 4 with the needles in the fully deployed position;

FIG. 6A is a view similar to FIG. 6, but shows the needle structure of FIG. 4A in the fully deployed position;

FIG. 7 is a view similar to FIGS. 4 and 6, which shows an alternative form of retaining the needles once deployed;

FIG. 7A is a view similar to FIG. 7, which shows the needle structure of FIG. 4A;

FIG. 8 is a view similar to FIG. 7, which shows the replacement capability of the needle retaining material;

FIG. 8A is a view similar to FIG. 7A, which shows the replacement capability of the needle retaining material;

FIG. 9 illustrates another alternative embodiment of the needle retaining feature of the instrument of the present invention;

FIG. 10 illustrates, in perspective view, another embodiment of the suturing instrument of the present invention;

FIG. 11 is an exploded view, with parts separated, of the embodiment of FIG. 10;

FIG. 12 is a partial cross-sectional view of the proximal end of the embodiment of FIG. 10;

FIG. 13 is a cross-sectional view taken along section line 13—13 of FIG. 12;

FIG. 14 is a view similar to FIG. 13 which shows the progressive movement of the lockout mechanism relative to FIG. 13 during the deployment operation of the instrument;

FIG. 15 is a cross-sectional view of the distal end of the embodiment of FIG. 10;

FIG. 16 is a top cross-sectional view taken along section line 16—16 of FIG. 15;

FIG. 17 is a cross-sectional view of the distal end of the embodiment of FIG. 10 which shows the needle carrier in the deployed position;

FIG. 18 is a top cross-sectional view taken along the section line 18—18 of FIG. 17;

FIG. 19 is another embodiment of the suturing instrument of the present invention;

FIG. 20 is another embodiment of the suturing instrument of the present invention; and FIG. 21 is another embodiment of the suturing instrument of the present invention;

FIG. 22 is another embodiment of the suturing instrument of the present invention;

FIG. 23 is an exploded view with parts separated of the instrument of FIG. 22;

FIG. 24 is an exploded view with parts separated of an alternate embodiment of the instrument of the present invention; and FIG. 25 is a cross-sectional view taken along the section line 25—25 of FIG. 24.

4

DETAILED DESCRIPTION OF THE PREFERRED EMBODIMENTS

Referring now in specific detail to the drawings, in which like reference numerals identify similar or identical elements throughout the several views, and initially to FIGS. 1–6, one embodiment of a suturing instrument for closing puncture wounds in accordance with the present invention is shown generally at 10. Suturing instrument 10 is particularly adapted for driving a pair of needles 12 and 14 from within the endoscopic cavity of a patient into the peripheral tissue adjacent an endoscopic puncture wound and placing a suture therein. However, instruments which utilize more or less than two needles are also within the scope of the present invention.

Generally, suturing instrument 10 includes an elongated housing portion, for example, elongated tubular body 16 having actuator button 18 slidably disposed at proximal end 20 and needle deploying means such as needle carrier arms 24 and 26 mounted adjacent distal end 28. Elongated tubular body 16 is suitable for insertion preferably through a trocar cannula or alternately directly into a puncture wound such as a trocar incision wound formed during an endoscopic or laparoscopic surgical procedure. Except where noted otherwise, the materials utilized in the components of the instrument generally include such materials as polycarbonate for housing sections and related components, and stainless steel, particularly for components which transmit forces. One preferred material is a polycarbonate material available from General Electric Company under the trade name LEXAN. Other specific preferred materials such as nylon or glass filled nylon (for strength) may also be utilized. However, equivalent alternative materials will readily come to the mind of those skilled in the art.

In FIG. 2, distal end 28 of instrument 10 is shown with the component parts separated for illustration purposes. Elongated housing portion 16 includes housing half-sections 16a and 16b which are attached by any suitable means, such as for example, fasteners, adhesives, welding, etc. A pair of needles such as curved needles 12 and 14 are removably mounted such as by slip fitting them to carrier arms 24 and 26, respectively. Carrier arms 24 and 26 are operatively mounted on elongated housing portion 16 in cut out portions 30a and 30b formed in housing half sections 16a and 16b, respectively. Carrier arms 24 and 26 are preferably pivotally mounted on posts 32 and 34 respectively.

An actuating member is provided, such as elongated rod 36 which is slidably positioned in a bore formed through elongated housing portion 16 and made up of grooves 38a (not shown) and 38b foraged in housing half-sections 16a and 16b, respectively. Preferably, grooves 38a and 38b conform in shape to the outer surface of elongated rod 36 so as to facilitate sliding motion of elongated rod 36 within elongated housing portion 16. Elongated rod 36 is provided with teeth 40 formed on both side edges of flattened distal end portion 42. In the illustrated embodiment, distal end portion 42 is shown as being flattened, having a rectangular cross-section. Clearly, any suitable cross-section may be substituted for flattened distal end portion 42 or for rod 36.

Teeth 40 of elongated rod 36 cooperate, i.e. mesh, with teeth 44 of carrier arms 24 and 26 in a rack and pinion fashion so as to cause carrier arms 24 and 26 to pivot about posts 32 and 34, respectively. Needle retaining means are also provided, such as latch member 46 which is inserted in cutout portions 48a (not shown) and 48b formed in housing half-sections 16a and 16b, respectively. A suture passageway is provided in elongated rod 36, as best seen in FIG. 3, shown as bore 50 formed along the central longitudinal axis of elongated rod 36 and passing therethrough from end to end. A suitable suture material such as suture 52 is thereby stored and fed through bore 50 and passes through distal end 28 at a bore made up of grooves 53a and 53b (FIG. 2) formed in housing half-sections 16a and 16b, respectively. Suture 52 is attached to proximal ends 54 and 56 of needles 12 and 14.

As shown in FIG. 3, elongated rod 36 is spring biased in a proximal direction corresponding to a retracted position of needles 12 and 14, illustrated in FIGS. 4 and 5. In the retracted position, needles 12 and 14 are preferably disposed completely within elongated housing portion 16. This facilitates insertion and removal of suturing instrument 10 without undesired contact of needle 12 and 14 with either the patient's tissue or that of the operating room personnel.

In operation, suturing instrument 10 is inserted in a puncture wound such as the type created by a trocar during endoscopic or laparoscopic surgical procedures. Preferably the instrument is inserted in the incision wound (in the direction of arrow A in FIG. 6) so that proximal end 58 of the opening formed by cutouts 30a and 30b is situated immediately below the fascia, designated as 60 in FIG. 6. Separate indicating means (not shown) may be provided on suturing instrument 10 to apprise the user as to when suturing instrument 10 is in the preferred position.

Alternatively, suturing instrument 10 may be inserted through an appropriately sized trocar situated in a body wall. Once suturing instrument 10 is adequately inserted, the trocar may be removed leaving suturing instrument 10 in place.

With suturing instrument 10 situated in the appropriate position, actuating button 18 (FIG. 1) is depressed thereby urging elongated rod 36 in a distal direction causing teeth 40 to rotate carrier arms 24 and 26, due to the meshing of teeth 40 with teeth 44 of the carrier arm gear mechanism. Curved needles 12 and 14 are thereby rotated such that pointed ends 62 and 64 pierce fascia 60 allowing the needles to pass through a portion of the fascia and surrounding tissue. (See arrow B in FIG. 6). Upon complete depression of actuator button 18, needles 12 and 14 become latched in latch member 46. One way of achieving the latching is shown as notched portions 65 and 67 of needles 12 and 14 engage hooked ends 69 and 71 of latch 46.

Actuator button 18 is released allowing elongated rod 36 to return to its proximal position and carrier arms 24 and 26 to return to their retracted positions within elongated housing portion 16 leaving needles 12 and 14 attached to latch member 46. Suturing instrument 10 is pulled out of the trocar incision causing suture 52 (still attached to needles 12 and 14 which are latched onto suturing instrument 10) to be pulled through fascia 60 following the path taken by needles 12 and 14 and up through the remainder of the trocar incision until exiting the opening at the surface of the skin. Suture 52 is grasped and preferably cut away from needles 12 and 14 and thereafter tied off in the appropriate surgeon's knot.

FIGS. 2A, 4A and 6A illustrate an alternative embodiment of the instrument illustrated in FIGS. 1–6. Suturing instrument 11 is structurally and operationally the same as suturing instrument 10 with a few exceptions which be the only details described hereinafter. The remaining structural and operational details of suturing instrument 11 are substantially identical as those for suturing instrument 10 as set forth in the description above. Instead of needles 12 and 14 as provided in suturing instrument 10, suturing instrument 11 is provided with suture carrying heads 13 and 15 which are removably mounted on pivotable arms 25 and 27, for example by way of ends 17 and 19 slip fitting into slotted bores 29 and 31 foraged at the ends of arms 25 and 27. Slotted bores 29 and 31 are slotted to allow for passage of suture 52 when suture carrying heads 13 and 15 are loaded on arms 25 and 27, respectively.

Instead of latch member 46, a unitary member as illustrated in FIG. 2 for suturing instrument 10, latch members 46a and 46b are provided to retain suture carrying heads 13 and 15 upon deployment thereof. In operation, instrument 11 is utilized in the same manner as set forth above, except that when suture carrying heads 13 and 15 are deployed, they become latched in latch members 46a and 46b, respectively. Arms 25 and 27 retract within the opening formed by cut-outs 30a and 30b formed on suturing instrument 11.

FIGS. 7 and 8 illustrate an alternative embodiment for retaining needles 12 and 14 within suturing instrument 10 after actuation thereof. Instead of latch member 46 as shown in the embodiment of FIGS. 1–6, a suitable compliant material, such as, SANTOPRENE® available from Monsanto, is inserted in the spaces created by cut-out sections 48a and 48b (FIG. 2). Upon actuation of suturing instrument 10, needles 12 and 14 become embedded in compliant material 66. The remainder of the suturing procedure is performed in the same fashion as described above for the embodiment of the present invention depicted in FIGS. 1–6.

After use of the suturing instrument of FIGS. 7 and 8, the needles may be removed along with the used compliant material 66, as shown in FIG. 8, from the spaces created by cut-out sections 48a and 48b. Those spaces may then be re-loaded with a new section of compliant material 66 and new needles attached to suture material which is loaded in place on suturing instrument 10. The process, described above, may then be repeated throughout the procedure. While it is intended that the suturing instrument of the present invention be disposable, it is also within the scope of the present invention that the device be re-usable by replacement of used components such as needles 12 and 14 and compliant materials 66 and the sterilization of the remainder of the instrument by known sterilization techniques.

FIGS. 7A and 8A illustrate file use of removable compliant material to retain suture carrying heads 13 and 15.

FIG. 9 illustrates another alternative embodiment of the embedding feature described for FIGS. 7 and 8. Collar 68 is shown in FIG. 9 disposed over the space created by cut outs 48a and 48b. Upon actuation of the suturing instrument, needles 12 and 14 pass through collar 68 which is made of a compliant material such as that used for compliant material 66. Once needles 12 and 14 pass through collar 68 they become embedded therein and the remainder of the suturing procedure is perforated as described for the embodiment on the instrument of FIGS. 1–6. Collar 68 can similarly be used to retain the suture carrying heads 13 and 15 of the embodiment of FIG. 2A.

Another embodiment of the suturing instrument of the present invention will now be described with reference to FIGS. 10–18 and initially with reference to FIG. 10 in conjunction with FIG. 11. Similar to the embodiment of FIGS. 1–9, suturing instrument 110 is particularly adapted for driving a pair of needles 112 and 114 from within the endoscopic cavity of a patient into the peripheral tissue adjacent an endoscopic puncture wound and placing a suture therein.

Generally, suturing instrument 110 includes an elongated housing portion, for example, elongated body 116. Actuator knob 118 is operatively disposed at proximal end 120 of suturing instrument 110 and is connected to elongated control rod 136 which passes through elongated body 116 formed by housing half-sections 116a and 116b. Elongated control rod 136 is connected at a distal end thereof to needle carrier 124. In the embodiment illustrated, needle carrier 124 is disposed adjacent distal end 128 of elongated body 116.

Needles 112 and 114 are held in place on needle carrier 124 by frictional fitting of the needles within peripheral groove 126. A ridge or raised portion (not shown) is preferably provided within peripheral groove 126 as a base for the suture receiving end of needles 112 and 114. The sharp ends of needles 112 and 114 are protected by their fitting into cut-out 130, recess 132 and cutout 134, recess 135, respectively, formed near the side edges of housing half-sections 116a and 116b. See also FIG. 15. Needles 112 and 114 are preferably separated by a constant distance defined by the diameter of needle carrier 124, when a round disc is used, or the distance across the needle carrying member, i.e., from needle to needle when any other geometric configuration is utilized as is shown by dimension "d" in FIG. 15.

A continuous suture passageway is formed from the communication of separate longitudinally aligned passageways, i.e. a bore formed through needle carrier 124, a bore extending through elongated control rod 136 and a bore formed through the central longitudinal axis of actuator knob 118. In this configuration, suture material such as suture 152 can be passed through the passageway so as to sufficiently store the suture material which is attached to needles 112 and 114.

A lock-out mechanism is also provided on suturing instrument 110, as best illustrated in FIG. 11, and includes spring biased pin 138 which is biased by spring 139 toward arcuate groove 140 formed on the distal face of actuator knob 118. The function of the lockout mechanism is two-fold. The first function is to provide seating points at either end of the operation cycle to maintain needle carrier 124 at either position. The second is to ensure the proper alignment of needles 112 and 114 with the elongated body 116 in the initial or stored position and in the desired fully deployed orientation, i.e., such that needles 112 and 114 are in a plane which is substantially perpendicular to the initial or stored position. Arcuate groove 140 has detent portions, for example, detents 142 and 148, as shown in FIGS. 12–14, which provide resistance to rotation of actuator knob 118 so that needle carrier 124 is not prematurely deployed or retracted when not intended by the user. Spring biased pin 138 preferably has spring biased extended portion 146 which fits into detents 142 and 148 of actuator knob 118. Detent 142 corresponds to the initial or stored position, wherein needle carrier 124 is substantially in the same horizontal plane as elongated body 116. In this configuration, spring biased pin 138 will maintain needle carrier 124 in the initial or stored position until the user desires to deploy needle carrier 124 by rotating actuator knob 118 in a counter-clockwise motion. Clearly, the instrument can be configured so as to deploy needle carrier 124 upon motion of actuator knob 118 in a clockwise motion. Detent 148 corresponds to the fully deployed position of the instrument wherein needle carrier 124 is substantially perpendicular to the initial or stored position. Thus, spring biased pin 138 will maintain needle carrier 124 in the fully deployed position until the user desires to retract needle carrier 124 by rotating actuator knob 118 in a clockwise motion.

In an alternative embodiment, detent 142, formed at the fully deployed position along arcuate groove 140, may be sufficiently wide to allow the entire width of spring biased pin 138 to enter, thereby permanently locking needle carrier 124 in the fully deployed position. In that position, needles 112 and 114 are substantially perpendicular to their originating position, at which actuator knob is situated such that spring biased pin 138 is seated in a detent formed at end 144 of arcuate groove 140. This position is shown in FIG. 12.

As shown in FIGS. 10, 11, 15 and 17, needle retaining means, such as slidable skin guard 150, are also provided with instrument 110 for receiving and retaining needles 112 and 114. A slot 153, FIG. 11, is formed through skin guard 150 and is configured to allow slidable passage of skin guard 150 over distal end 128 of elongated body 116. Slot 154, is configured to receive the needles. Knurled collar 156 is disposed at the proximal end of skin guard 150 to provide a gripping surface when instrument 150 is inserted in the puncture wound to be sutured. Knurled collar 156 also prevents suturing instrument 150 from being inserted too far within the incision. Specifically, flange portion 151 rests on the surface of the skin peripheral to the trocar wound, as shown in FIGS. 15 and 17. Space 158 is formed to receive compliant material 159 which may be made from SANTOPRENE®, or any other suitable material. As can be seen, compliant material 159 protrudes outwardly from space 158.

Alternatively, a mechanical latching mechanism may be provided wherein needles 112 and 114 become mechanically retained in skin guard 150. In such an embodiment, needles 112 and 114 may be provided with barbs as shown in the embodiment of FIG. 6 so as to mechanically latch with a suitable member.

In operation, suturing instrument 110 is preferably inserted directly into a puncture wound such as a trocar incision wound, preferably with skin guard 150 covering needles 112 and 114, as shown in FIG. 15, until collar 156 of skin guard 150 rests against the peripheral tissue at the entrance to the puncture wound. Skin guard 150 is held with one hand and suturing instrument 110 is urged distally until needles 112 and 114 are positioned below fascia 160, as shown in FIG. 17.

Actuator knob 118 is rotated in a counter-clockwise fashion (when looking at the proximal end of suturing instrument from outside the puncture wound) until no further rotation is possible. This is because spring loaded pin 138 travels in arcuate groove 140 from detent 142 to detent 148. Spring loaded pin 138 makes contact with the wall of arcuate groove 140 which prevents further counter-clockwise rotation of actuator knob 118. Needle carrier 124, thereby, rotates counter-clockwise to a position substantially perpendicular to its initial position (FIG. 16), as shown in FIGS. 17 and 18. While holding skin guard 150 in place, suturing instrument 110 is pulled proximally towards the opening of the trocar incision wound so that needles 112 and 114 pass through fascia 160 and become embedded in compliant material 159 of skin guard 150. Skin guard 150 is pulled proximally to separate needles 112 and 114 from needle carrier 124. Skin guard 150 is then pulled proximally, while suturing instrument 110 is held in place to release needles 112 and 114 to skin guard 150. Instrument 110 is then removed from the trocar incision thereby exposing suture 52 so that the user may cut suture 52 away from needles 112 and 114 and tie the appropriate knot.

FIGS. 19–21 illustrate the other alternative embodiments of the suturing instrument of the present invention. In FIG. 19, suturing instrument 210 is particularly adapted for driving a pair of needles 212 and 214 from within the endoscopic cavity of a patient into the peripheral tissue adjacent an endoscopic puncture wound and placing a suture therein as set forth for the previously discussed embodiments.

Suturing instrument 210 is provided with a shield member such as elongated hollow tubular member 216 having needle retaining means, for example, needle retaining pockets 212 and 214 disposed along the inner surface thereof. Needle retaining pockets 218 and 220 may be configured such that needles 212 and 214 become frictionally retained therein upon insertion of the needles. Alternatively, a compliant material may be filled in needle retaining pockets 218 and 220 such that upon insertion, needles 212 and 214 become lodged therein. Needle carrier 224 is provided and functions in the same manner as needle carrier 124 of the embodiment described in association with FIGS. 10–18 above. Similarly, the suture carrying and passage is the same as that described above.

In operation, suturing instrument 210 is preferably inserted through a trocar cannula or alternately directly into a puncture wound, such as a trocar incision wound. During insertion, elongated hollow tubular member 216, which is slidably mounted on elongated control rod 236, is situated in a position so as to cover needles 212 and 214. However, during insertion, elongated hollow tubular member 216 is oriented such that needles 212 and 214 are not aligned with needle retaining pockets 218 and 220. Upon adequate insertion of suturing instrument 210, the trocar cannula is removed.

Once suturing instrument is inserted deep enough into the incision so that needles 212 and 214 are positioned below the fascia, as described and shown for the previously described embodiments, elongated hollow tubular member 216 is moved proximally towards handle 222, while handle 222 is maintained stationary with respect to the incision. When distal end 228 of elongated hollow tubular member 216 passes to a position proximal of the fascia, the tissue on the periphery of the inner portion of the incision will tend to close around distal end 228.

Elongated hollow tubular member is rotated so as to align needle retaining pockets 218 and 220 with needles 212 and 214, respectively. Rotation limiting means such as that described above, i.e. the lockout mechanism of the embodiment of FIGS. 10–18, may also be provided in the presently described embodiment in order to assure alignment of the needles with the needle retaining pockets. When the desired alignment is attained, handle 222 is pulled proximally while elongated hollow tubular member 216 is held stationary until no further travel is possible. Needles 212 and 214 thus penetrate the fascia which close around distal end 228 and become embedded in needle retaining pockets 218 and 220, respectively. In one embodiment, needle retaining pockets 218 and 220 are dimensioned such that needles 212 and 214 become embedded due to friction fitting in the pockets.

In another embodiment, needle retaining pockets 218 and 220 may be provided with compliant material, such as SANTOPRENE®, such that needles 212 and 214 become embedded in the compliant material. Alternatively, mechanical latching means may be provided on suturing instrument 210 to retain needles 212 and 214 upon deployment thereof.

Elongated hollow tubular body 216 is then pulled proximally, while handle 222 is held stationary. This action pulls needles 212 and 214 away from needle carrier 224. With continued proximal pulling of elongated tubular body 216, needles 212 and 214 and, thereby suture 252 are pulled to the outer surface of the trocar wound. The surgeon grasps the suture near its connection to each of the needles, cuts it and pulls the suture up and outside to the surface of the incision. Suturing instrument 210 is removed by pulling the whole assembly out of the wound and the process repeated as set forth above by reloading it with a fresh suture and needle.

FIG. 20 illustrates suturing instrument 310 which is another embodiment of the suturing instrument of the present invention. However, suturing instrument 310 operates in a somewhat different way than the previously described embodiments. For example, elongated hollow tubular member does not have needle retaining pockets disposed thereon. Instead, needles 312 and 314 are provided with suture receiving holes near their puncturing or pointed ends.

The following description will focus on the features of the operation of suturing instrument 310 which differ from those of the previously described embodiments. Suturing instrument 310 is inserted in the puncture wound with elongated hollow tubular member 316 covering needles 312 and 314 and some or all of needle carrier 324. When distal end 328 passes below the inner surface of the fascia, elongated hollow tubular member 316 is moved proximally, similar to that described above for the embodiment of FIG. 19. Tissue enters between the open space (Arrow C) between distal end 328 and the tips of needles 312 and 314. Instead of moving elongated hollow tubular member 316 back over needles 312 and 314, handle 322 is pulled proximally, thereby urging needles 312 and 314 to pierce the tissue around the periphery of the inner surface of the fascia.

In order to protect the skin from the tips of needles 312 and 314 as handle 322 is pulled proximally, elongated hollow tubular member 3 16 is held just below the surface of the skin. Suture 352 is grasped when needles 312 and 314 emerge from the incision, removed from needles 312 and 314 and pulled to the surface of the wound. Handle 322 is urged distally, reversing the preceding travel path so that needles 312 and 314 become freed from the tissue. Elongated hollow tubular member 316 is moved distally to cover needles 312 and 314 and suturing instrument 310 is pulled proximally out of the wound. Suture 352 is tied with the appropriate knot and the procedure repeated as necessary or desired.

Needles 312 and 314 preferably are fixed within needle carrier 324, however, it is within the scope of the invention for the needles to be removable and replaced with fresh needles or the fixed needles may be re-threaded with fresh suture so that the instrument may be reused.

FIG. 21 illustrates another embodiment of the suturing instrument of the present invention which functions in the same manner as described for suturing instrument 310. For example shield 416 operates in the same manner as elongated hollow tubular member 316, described above. However, since instrument 410 has a single needle 412, the operation of pulling instrument 410 proximally so that needle 412 passes through the tissue which enters between elongated hollow member 410 and the tip of needle 412, must be repeated. Suturing instrument 410 is preferably twisted approximately 180° before repeating the proximal pulling of the instrument to pass needle 412 through the tissue a second time. Otherwise, suture 452 is placed in the same manner as suture 352 and the instrument is removed in the same manner once the suture is in place.

FIGS. 22–23 illustrate another alternative embodiment of the present invention. Suturing instrument 510 is somewhat similar to suturing instrument 110 of FIGS. 10–18. However, instead of being provided with a skin guard such as skin guard 150 as is best shown in FIG. 11, suturing instrument 510 is provided with sliding needle trap member 550. To accommodate needle trap member 550, suturing instrument 510 is provided with through slots 560 formed in housing split-half sections 516a and 516b which receive raised slide guides 562 foraged on or attached to needle trap member half section 550b. Corresponding receiving slots 564 are formed in needle trap member half section 550a to receive raised slide guides 562. Split sections 550a and 550b may be removably attached or raised slide guides 562 may be securely attached to receiving slots 564 by adhesives or other suitable known bonding techniques. Half sections 550a and 550b may also be connected by other means such as by wrapping them around housing 516.

Preferably split-half sections 550a and 550b are semi-circular in cross section and have a sloped distal end 568 which conforms to sloped portions 570 of split half-sections 516a and 516b of suturing instrument 510. This configuration is desirable to facilitate insertion of suturing instrument 510 through a trocar incision wound with or without a trocar cannula in place therein.

In operation, suturing instrument 550, having sliding needle trap member 550 works in the same manner as set forth above for the embodiment illustrated in FIGS. 10–18. Sliding needle trap member 550 is further provided with depressions 566 formed on the outer surface of half-sections 550a and 550b near the proximal end thereof to facilitate gripping by the fingers of the instrument operator.

Another embodiment of the needle trap member is shown in FIGS. 24 and 25 wherein slidable needle trap member 580 has a positive locking feature incorporated therein. In particular, strip trap 582 is provided on the distal end of slidable needle trap member 580. Strip trap 582 has slot 584 formed thereon at the distal end. Slot 584 is positioned such that upon rotation of needles 512 and 514 into their deployed position, the tips of needles 512 and 514 are in longitudinal alignment with slot 584. In this orientation, when suturing instrument is pulled proximally and slidable needle trap member 580 is held in place, needles 512 and 514 enter into slot 584 of strip trap 582 to engage latch 589. That is, needles 512 and 514 are preferably provided with barbs 586 and 588 at their tips to engage the latch for retention in slot 584.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above but not limited thereto, are to be considered within the scope of the invention.

What is claimed is:

1. A surgical instrument for applying sutures, which comprises:
   a) a shaft;
   b) a needle carrier connected to a distal end portion of said shaft;
   c) a needle having a tapered end portion and a base portion, said base portion disposed in said needle carrier such that at least said needle base portion is spaced a fixed predetermined distance from a central longitudinal axis of said instrument; and
   d) an elongated housing member surrounding said shaft and being longitudinally slidable thereon to a distally extended position, wherein said needle is at least partially enclosed within said elongated housing member by said elongated housing member moving from said tapered end portion toward said base portion such that said tapered end portion is shielded from body tissue by said elongated housing member, and to a proximally extended position, wherein said needle tapered end portion is exposed to such body tissue.

2. A surgical instrument for applying sutures, according to claim 1, which further comprises a needle retaining structure attached to said elongated housing, wherein when said elongated housing is moved to said first position and said tapered end portion axially aligned with said needle retaining structure, said tapered portion of said needle is retained in said retaining structure.

3. A surgical instrument for applying sutures, according to claim 1, wherein said needle tapered end portion defines a suture receiving opening therein.

4. A surgical instrument for applying sutures according to claim 3, which further comprises a suture material having one end thereof passed through said needle and which is contained in a suture passageway formed longitudinally through said shaft.

5. A surgical instrument for applying sutures, according to claim 1, which further comprises a handle connected to a proximal end portion of said shaft.

6. A surgical instrument for applying sutures, according to claim 5, wherein said handle includes a finger loop to facilitate movement of said shaft.

7. A surgical instrument for applying sutures, according to claim 6, which further comprises a grip portion disposed at a proximal end portion of said elongated housing to facilitate relative longitudinal movement of said shaft and said elongated housing.

8. A surgical instrument for applying sutures, which comprises:
   a) a shaft;
   b) a needle carrier connected to a distal end portion of said shaft;
   c) a needle having a tapered end portion and a base portion, said base portion disposed in said needle carrier such that said needle is spaced a fixed predetermined distance from said shaft, wherein said needle tapered end portion defines a suture receiving opening therein;
   d) a suture material having one end thereof passed through said needle and which is contained in a suture passageway formed longitudinally through said shaft; and
   e) an elongated housing member surrounding said shaft and being longitudinally slidable thereon between a distally extended position, wherein said needle is at least partially enclosed within said elongated housing member such that said tapered end portion is shielded from body tissue by said elongated housing member, and a proximally extended position, wherein said needle tapered end portion is exposed to such body tissue.

9. A surgical instrument for applying sutures, according to claim 8, which further comprises a needle retaining structure attached to said elongated housing, wherein when said elongated housing is moved to said distally extended position and said tapered end portion axially aligned with said needle retaining structure, said tapered portion of said needle is retained in said retaining structure.

10. A surgical instrument for applying sutures, according to claim 8, which further comprises a handle connected to a proximal end portion of said shaft.

11. A surgical instrument for applying sutures, according to claim 10, wherein said handle includes a finger loop to facilitate movement of said shaft.

12. A surgical instrument for applying sutures, according to claim 8, which further comprises a grip portion disposed at a proximal end portion of said elongated housing to facilitate relative longitudinal movement of said shaft and said elongated housing.

13. A surgical instrument for applying sutures, which comprises:

a) a shaft;

b) a needle carrier connected to a distal end portion of said shaft;

c) a needle having a tapered end portion and a base portion, said base portion disposed in said needle carrier such that said needle is spaced a fixed predetermined distance from a central longitudinal axis of said instrument;

d) an elongated housing member surrounding said shaft and being longitudinally slidable thereon between a distally extended position, wherein said needle is at least partially enclosed within said elongated housing member such that said tapered end portion is shielded from body tissue by said elongated housing member, and a proximally extended position, wherein said needle tapered end portion is exposed to such body tissue; and e) a needle retaining structure attached to said elongated housing, wherein when said elongated housing is moved to said distally extended position and said tapered end portion axially aligned with said needle retaining structure, said tapered portion of said needle is retained in said retaining structure.

14. A surgical instrument for applying sutures, according to claim 13, wherein said needle tapered end portion defines a suture receiving opening therein.

15. A surgical instrument for applying sutures, according to claim 14, which further comprises a handle connected to a proximal end portion of said shaft.

16. A surgical instrument for applying sutures, according to claim 13, which further comprises a handle connected to a proximal end portion of said shaft.

17. A surgical instrument for applying sutures, according to claim 16, wherein said handle includes a finger loop to facilitate movement of said shaft.

18. A surgical instrument for applying sutures, according to claim 17, which further comprises a grip portion disposed at a proximal end portion of said elongated housing to facilitate relative longitudinal movement of said shaft and said elongated housing.

* * * * *